United States Patent [19]

Tracz

[11] Patent Number: 5,686,599
[45] Date of Patent: Nov. 11, 1997

[54] SYNTHESIS, DEPROTECTION, ANALYSIS AND PURIFICATION OF RNA AND RIBOZYMES

[75] Inventor: Danuta Tracz, Boulder, Colo.

[73] Assignee: Ribozyme Pharmaceuticals, Inc., Boulder, Colo.

[21] Appl. No.: 432,876

[22] Filed: May 2, 1995

Related U.S. Application Data

[60] Division of Ser. No. 380,734, Jan. 30, 1995, which is a continuation-in-part of Ser. No. 345,516, Nov. 28, 1994, abandoned, which is a continuation-in-part of Ser. No. 245,736, May 18, 1994, abandoned, which is a continuation-in-part of Ser. No. 167,586, Dec. 14, 1993, abandoned, which is a continuation-in-part of Ser. No. 884,436, May 14, 1992, abandoned.

[51] Int. Cl.$^6$ ............................ C12P 19/34; C07H 21/00; C07H 21/02
[52] U.S. Cl. ................. 536/25.31; 435/91.1; 536/26.71; 536/25.3; 536/23.1
[58] Field of Search ........................ 435/91.1, 174; 536/26.71, 25.31, 25.3

[56] References Cited

U.S. PATENT DOCUMENTS

| | | | |
|---|---|---|---|
| 4,661,450 | 4/1987 | Kemp et al. | 435/91.41 |
| 4,851,331 | 7/1989 | Vary et al. | 435/6 |
| 4,987,071 | 1/1991 | Cech et al. | 435/91.31 |
| 5,064,754 | 11/1991 | Mills et al. | 435/6 |
| 5,116,742 | 5/1992 | Cech et al. | 435/91.31 |
| 5,180,818 | 1/1993 | Cech et al. | 536/23.1 |
| 5,348,868 | 9/1994 | Reddy et al. | |

FOREIGN PATENT DOCUMENTS

| | | |
|---|---|---|
| 0360257 | 3/1990 | European Pat. Off. |
| 2195883 | 8/1990 | Japan |
| 3228676 | 10/1991 | Japan |
| 9013641 | 11/1990 | WIPO |
| 9103162 | 3/1991 | WIPO |
| 9104319 | 4/1991 | WIPO |
| 9104324 | 4/1991 | WIPO |
| 9110453 | 7/1991 | WIPO |
| 9115880 | 7/1991 | WIPO |
| 9118913 | 12/1991 | WIPO |
| 9207065 | 4/1992 | WIPO |
| 9402595 | 2/1994 | WIPO |

OTHER PUBLICATIONS

Gasparutto, D. "Chemical Synthesis of a Biologically Acive Natural tRNA with its Minor Bases". NAR vol. 20 No. 19 1992.

Ballantyne et al., "Nucleotide sequence of the cDNA for murine intercellular adhesion molecule-1 (ICAM-1)," *Nucleic Acids Research* 17:5853 (1989).

Barinaga, "Ribozymes: Killing the Messenger," *Science* 262:1512–1514 (1993).

Cotten, "The in vivo application of ribozymes," *TIBTECH* 8:174–178 (1990).

Edgington, "Ribozymes: Stop Making Sense," *Biotechnology* 10:256–262 (1992).

Kita et al., "Sequence and expression of rat ICAM-1," *Biochem. Biophys. Acta* 1131:108–110 (1992).

Simons et al., "ICAM, an adhesion ligand of LFA-1, is homologous to the neutral cell adhesion molecule NCAM," *Nature* 331:624–627 (1988).

Usman and Cedergren, "Exploiting the chemical synthesis of RNA," *TIBS* 17:334–339 (1992).

Andrus et al., ACS National Meeting, New York, Apr. 18, 1986k, Org. Chem. Div. Abstr. 333 as cited in Wright et al. *Tetrahedron Lett.* 34;3373–3376 (1993).

Arnold et al., "Automated Chloridite and Amidite Synthesis of Oligodeoxyribonucleotides on a Long Chaim Support Using Amidine Protected Purine Nucleosides," *Collect. Czech. Chem. Commun.* 54:523–532 (1989).

Auer et al., "Synthesis and Biological Applications of 2',3'-Dideoxynucleoside-5'-(O-(α-Thio)Triphosphates," *Nucleosides & Nucleotides* 8:849 (1989).

Beacuage and Iyer, *Tetrahedron Lett.* 49:6123 (1991).

Bhat et al., "An Improved Synthesis of 2',3'-Dideoxycytidine," *Nucleosides & Nucleotides* 9:1061 (1990).

Cameron and Jennings, "Specific Gene Expression by Engineered Ribozymes in Monkey Cells," *Proc. Natl. Acad. Sci. USA* 86:9139–9143 (1989).

Cech, "Ribozymes and Their Medical Implications," *JAMA* 260:3030–3034 (1988).

Chang et al., "Ribozyme–Mediated Site–Specific Cleavage of the HIV-1 Genome," *Clinical Biotechnology* 2:23–31 (1990).

Chu et al., "General Syntheses of 2',3'-Dideoxynucleosides and 2',3'-Didehydro-2',3'-Dideoxynucleosides," *J. Org. Chem.* 54:2217 (1989).

Collins and Olive, "Reaction Conditions and Kinetics of Self–Cleavage of a Ribozyme Derived From Neurospora VS RNA," *Biochemistry* 32:2795–2799 (1993).

Dropulic et al., "Functional Characterization of a U5 Ribozyme: Intracellular Suppression of Human Immunodeficiency Virus Type I Expression," *Journal of Virology* 66:1432–1441 (1992).

Froehler and Matteucci, "Substituted 5–Phenhltetrazoles: Improved Activators of Deoxynucleoside Phosphormaidites in Deoxyoligonucleotide Synthesis," *Tetrahedron Lett.* 24:3171–3174 (1983).

Fourrey et al, "Improved Procedure for the Preparation of Deoxynucleoside Phosphoramidites: Arylphosphoramidites as New Convenient Intermediates for Oligodeoxynucleotide Synthesis," *Tetrahedron Lett.* 25:4511–4514 (1987).

Gait et al., *Nucleic Acids Research* 10:6243–6254 (1982).

Gao et al., "Transient Protection. 2. One–Flask Synthesis of 6–O–[(4–Nitrophenyl)ethyl]–2'–deoxyguanosine Nucleosides," *J. Org. Chem.* 51:755 (1986).

(List continued on next page.)

*Primary Examiner*—George G. Elliott
*Assistant Examiner*—Sean McGarry
*Attorney, Agent, or Firm*—Lyon & Lyon LLP

[57] ABSTRACT

Method for purification and synthesis of RNA molecules and enzymatic RNA molecules in enzymatically active form.

3 Claims, 17 Drawing Sheets

OTHER PUBLICATIONS

Guerrier-Takada et al., "The RNA Moiety of Ribonuclease P Is the Catalytic Subunit of the Enzyme," *Cell* 35:849–857 (1983).

Hampel et al., "RNA Catalyst for Cleaving Specific RNA Sequences," filed Sep. 20, 1989, which is a Continuation-in-Part of U.S. Serial No. 07/247,100 filed Sep. 20, 1988.

Hampel and Tritz, "RNA Catalytic Properties of the Minimum (−)s TRSV Sequence," *Biochemistry* 28:4929–4933 (1989).

Hampel et al., "'Hairpin' Catalytic RNA Model: Evidence for Helices and Sequence Requirement for Substrate RNA," *Nucleic Acids Research* 18:299–304 (1990).

Haseloff and Gerlach, "Simple RNA Enzymes with New and Highly Specific Endoribonuclease Activites," *Nature* 334:585–591 (1988).

Haupt et al., *Journal of Chromotography* 260:419–427 (1983).

Heidenreich and Eckstein, "Hammerhead Ribozyme-mediated Cleavage of the Long Terminal Repeat RNA of Human Immunodeficiency Virus Type 1," *Journal of Biological Chemistry* 267:1904 (1992).

Herdewijn et al., "Synthesis and Anti–HIV Activity of Different Sugar-Modified Pyrimidine and Purine Nucleosides," *J. Med. Chem.* 31:2040 (1988).

Hering et al., "Preparation and Properties of Chloro–N,N–dialkylamino–2,2,2–trichloroethoxy–and Chloro–N,N–dialkylamino–2,2,2–trichloro–1,1–dimethylethoxyphosphines and their Deoxynucleoside Phosphiteamidates," *Nucleosides and Nucleotides* 4;169–171 (1985).

Holy, "3'–O–Acetyl–2'–Deoxyadenosine," Ed. Zorbach and Tipson, *Synthetic Procedures in Nucleic Acid Chemistry* 1:172 (1968).

Huang and Chu, "A Practical Synthesis of 2'–Deoxyuridine from Uridine," *Synthetic Communications* 20:1039 (1990).

Imazawa and Eckstein, *J. Org. Chem.* 12:2039 (1979).

Jain et al., "Reactions of 2–Acyloxyisobutyryl Halides with Nucleosides. IV. A Facile Synthesis of 2',3',–Unsaturated Nucleosides Using Chromous Acetate," *J. Org. Chem.* 39:30 (1974).

Jeffries and Symons, "A Catalytic 13–mer Ribozyme," *Nucleic Acids Research* 17:1371–1377 (1989).

Kaskar and Markovac, "A New Synthesis of 2',3'–Dideoxycytidine", *J. Hetrocyclic Chem.* 26:1531 (1989).

Kawasaki et al., *J. Med. Chem.* (1992).

Kim and Cech, "Three–dimensional model of the active site of the self–splicing rRNA precursor of Tetrahymena," *Proc. Natl. Acad. Sci. USA* 84:8788 (1987).

Kovacs and Otvos, "Simple Synthesis of 5–Vinyl–and 5–Ethynyl–2'–Deoxyuridine–5'–Triphosphates," *Tetrahedron Lett.* 29:4525 (1988).

Ludwig, "A New Route to Nucleoside 5'–Triphosphates," *Acta Biochim. Biophys. Acad. Sci. Hung.* 16:131 (1981).

Ludwig and Eckstein, "Rapid and Efficient Synthesis of Nucleoside 5'–O–(1–Thiotriphosphates), 5'–Triphosphates and 2',3'–Cyclophosphorothioates Using 2–Chloro–4H–1,3, 2–Benzodioxaphosphorin–4–one," *J. Org. Chem.* 54:631 (1989).

Mamone et al., "Design of Hammerhead Ribozymes Targeted to Sequences in HIV, HSV and the RAT ANF Gene," Abstract of Keystone, CO (May 27, 1992).

McCarthy, Jr. et al., "Purine Nucleosides. XIV. Unsaturated Furanosyl Adenine Nucleosides Prepared via Base–Catalyzed Elimination Reactions of 2'–Deoxyadenosine Derivatives," *J. Amer. Chem. Soc.* 88:1549 (1966).

Morvan et al., *Tetrahedron Lett.* 31:7149 (1990).

Odai et al., "The role of a conserved guanosine residue in the hammerhead-type RNA enzyme," *FEBS* 267:150–152 (1990).

Odai et al., "Synthesis and NMR Study of Ribooligonucleotides Forming a Hammerhead-type RNA Enzyme System," *Nucleic Acids Research* 18:5955 (1990).

Pavco et al., "Regulation of Self–Splicing Reactions by Antisense RNA," Abstract of Keystone, CO (May 27, 1992).

Perreault et al., "Relationship between 2'–Hydroxyls and Magensium Binding in the Hammerhead RNA Domain: A Model for Ribozyme Catalysis," *Biochemistry* 30:4020–4025 (1991).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pon, "Enchanced Coupling Efficiency using 4–Dimethylaminopyridine (DMAP) and either Tetrazole, 5–(o–nitrophenyl) tetrazole, or 5–(p–nitrophenyl) tetrazole in the sold phoase synthesis of oligoribonucleotides by the phosphoramidite procedure," *Tetrahedron Lett.* 28:3643–3646 (1987).

Prisbe and Martin, "A Novel and Efficient Preparation of 2',3'–Dideoxynucleosides," *Synthetic Communications* 15:401 (1985).

Rossi et al, "Ribozymes as Anti–HIV–1 Therapeutic Agents: Principles, Applications, and Problems," *Aids Research and Human Retroviruses* 8:183–189 (1992).

Sambrook et al., *Molecular Cloning: A Laboratory Manual,* published by Cold Spring Harbor Laboratory Press (NY) pp. 7.71–7.78 (1989).

Sanger et al., "DNA Sequencing with Chain–Terminating Inhibitors," *Proc. Natl. Acad. Sci. USA* 74:5463 (1977).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA in Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Slim and Gait, "Configurationally Defined Phosphorothioate-Containing Oligoribonucleotides in the Study of the Mechanism of Cleavage of Hammerhead Ribozymes," *Nucleic Acids Research* 19:1183–1188 (1991).

Starrett, Jr., et al., "The Use of Acetyl Bromide for the Multigram Synthesis of the Anti–HIV Agent 2',3'-Didehydro–2',3'-Dideoxycytidine (d4C)," *Nucleosides & Nucleotides* 9:885 (1990).

Stec et al., "Sterochemical Studies of the formation of chiral internucleotide linkages by phosphoramidite coupling in the synthesis of oligodeoxyribonucleotides," *Tetrahedron. Lett.* 25:5279–5282 (1984).

Taylor and Rossi, "Ribozyme–Mediated Cleavage of an HIV–1 gag RNA: The Effects of Nontargeted Sequences and Secondary Structure on Ribozyme Cleavage Activity," *Antisense Res. and Dev.* 1:173–186 (1991).

Tsukiyama–Kohara et al., "Internal Ribosome Entry Site Within Hepatits C Virus RNA," *Journal of Virology* 66:1476–1483 (1992).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosporamidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Vu and Hirschbein, *Tetrahedron Lett.* 31:3005 (1991).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–5534 (1994).

Wright et al., "Large Scale Synthesis of Oligonucleotides via Phosphoramidite Nucleosides and a High–loaded Polystyrene Support," *Tetrahedron Lett.* 34:3373–3376 (1993).

Woolf et al., "Specificity of Antisense Oligonucleotides in vivo," *Proc. Natl. Acad. Sci. USA* 89:7305–7309 (1992).

Wyrzykiewicz and Ravikumar, *Bioorganic Med. Chem.* 4:1519 (1994).

Yanagawa et al., (1990) *Biochemistry* 29:10587–10589 (1990).

Zaug et al., *Science* 224:534 (1984).

DMF    Ac    Bz    i-Bu

R = H = PAC

R = tBu = TAC

R = iPr = iPPAC

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any base.
        The letter "H" stands for C, A or U.

( x i ) SEQUENCE DESCRIPTION: SEQ ID NO: 1:

NNNNUHNNNN N (2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO: 2:

NNNNNCUGAN GAGNNNNNNC GAAANNNN (2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.
            The letter "Y" stands for U or C.
            The letter "H" stands for A, U or C.

(xi) SEQUENCE DESCRIPTION: SEQ ID NO: 3:

NNNNNNNYNG HYNNN (2) INFORMATION FOR SEQ ID NO: 4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO: 4:

NNNNGAAGNN NNNNNNNNA AAHANNNNNN NACAUUACNN NNNNNNN (2) INFORMATION FOR SEQ ID NO: 5:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 5:

UGGCCGGCAU GGUCCCAGCC UCCUCGCUGG CGCCGGCUGG GCAACAUUCC GAGGGGACCG    60

UCCCCUCGGU AAUGGCGAAU GGGAC    85

(2) INFORMATION FOR SEQ ID NO: 6:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (xi) SEQUENCE DESCRIPTION: SEQ ID NO: 6:

-continued

| GGGAAAGCUU | GCGAAGGGCG | UCGUCGCCCC | GAGCGGUAGU | AAGCAGGGAA | CUCACCUCCA | 60 |
| AUUUCAGUAC | UGAAAUUGUC | GUAGCAGUUG | ACUACUGUUA | UGUGAUUGGU | AGAGGCUAAG | 120 |
| UGACGGUAUU | GGCGUAAGUC | AGUAUUGCAG | CACAGCACAA | GCCCGCUUGC | GAGAAU | 176 |

SYNTHESIS, DEPROTECTION, ANALYSIS AND PURIFICATION OF RNA AND RIBOZYMES

This application is a division of Usman et al., U.S. Ser. No. 08/380,734, filed Jan. 30, 1995, (hereby incorporated by reference herein in totality, including drawings) which is a continuation-in-part of two applications by Usman et al., both entitled "Synthesis, deprotection, analysis and purification of RNA and ribozymes" and filed on Nov. 28, 1994 as U.S. Ser. No. 08/345,516, now abandoned, and on May 18, 1994, as U.S. Ser. No. 08/245,736 now abandoned, which is a continuation-in-part of Dudycz et al. entitled "Preparation of purified ribozymes in sodium, potassium or magnesium salt form", filed Dec. 14, 1993, U.S. Ser. No. 08/167,586 (abandoned), which is a continuation of Dudycz et al. entitled "Preparation of purified ribozymes in sodium, potassium or magnesium salt form", filed May 14, 1992, U.S. Ser. No. 07/884,436 (abandoned). All of these prior applications are hereby incorporated by reference herein (including drawings).

BACKGROUND OF THE INVENTION

This invention relates to the synthesis, deprotection, and purification of enzymatic RNA or modified enzymatic RNA molecules in milligram to kilogram quantities with high biological activity.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. After the discovery of introns, two questions immediately arose: i) why are introns present in genes in the first place, and ii) how do they get removed from the RNA prior to protein synthesis? The first question is still being debated, with no clear answer yet available. The second question, how introns get removed from the RNA, is much better understood after a decade and a half of intense research on this question. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. They had chosen *Tetrahymena thermophila* as a matter of convenience, since each individual cell contains over 10,000 copies of one intron-containing gene (the gene for ribosomal RNA). They reasoned that such a large number of intron-containing RNA molecules would require a large amount of (protein) splicing factors to get the introns removed quickly. Their goal was to purify these hypothesized splicing factors and to demonstrate that the purified factors could splice the intron-containing RNA in vitro. Cech rapidly succeeded in getting RNA splicing to work in vitro, but something unusual was going on. As expected, splicing occurred when the intron-containing RNA was mixed with protein-containing extracts from Tetrahymena, but splicing also occurred when the protein extracts were left out. Cech proved that the intervening sequence RNA was acting as its own splicing factor to snip itself out of the surrounding RNA. They published this startling discovery in 1982. Continuing studies in the early 1980's served to elucidate the complicated structure of the Tetrahymena intron and to decipher the mechanism by which self-splicing occurs. Many research groups helped to demonstrate that the specific folding of the Tetrahymena intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the Tetrahymena intron could carry out a variety of cutting and joining reactions on tither pieces of RNA. The demonstration proved that the Tetrahymena intron can act as a true enzyme: i) each intron molecule was able to cut many substrate molecules while the intron molecule remained unchanged, and ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties. Also in 1986, Cech showed that the RNA substrate sequence recognized by the Tetrahymena ribozyme could be changed by altering a sequence within the ribozyme itself. This property has led to the development of a number of site-specific ribozymes that have been individually designed to cleave at other RNA sequences. The Tetrahymena intron is the most well-studied of what is now recognized as a large class of introns, Group I introns. The overall folded structure, including several sequence elements, is conserved among the Group I introns, as is the general mechanism of splicing. Like the Tetrahymena intron, some members of this class are catalytic, i.e. the intron itself is capable of the self-splicing reaction. Other Group I introns require additional (protein) factors, presumably to help the intron fold into and/or maintain its active structure. While the Tetrahymena intron is relatively large, (413 nucleotides) a shortened form of at least one other catalytic intron (SunY intron of phage T4, 180 nucleotides) may prove advantageous not only because of its smaller size but because it undergoes self-splicing at an even faster rate than the Tetrahymena intron.

Ribonuclease P (RNAseP) is an enzyme comprised of both RNA and protein components which are responsible for converting precursor tRNA molecules into their final form by trimming extra RNA off one of their ends. RNAseP activity has been found in all organisms tested, but the bacterial enzymes have been the most studied. The function of RNAseP has been studied since the mid-1970s by many labs. In the late 1970s, Sidney Altman and his colleagues showed that the RNA component of RNAseP is essential for its processing activity; however, they also showed that the protein component also was required for processing under their experimental conditions. After Cech's discovery of self-splicing by the Tetrahymena intron, the requirement for both protein and RNA components in RNAseP was reexamined. In 1983, Altman and Pace showed that the RNA was the enzymatic component of the RNAseP complex. This demonstrated that an RNA molecule was capable of acting as a true enzyme, processing numerous tRNA molecules without itself undergoing any change. The folded structure of RNAseP RNA has been determined, and while the sequence is not strictly conserved between RNAs from different organisms, this higher order structure is. It is thought that the protein component of the RNAseP complex may serve to stabilize the folded RNA in vivo At least one RNA position important both to substrate recognition and to determination of the cleavage site has been identified, however little else is known about the active site. Because tRNA sequence recognition is minimal, it is clear that some aspect(s) of the tRNA structure must also be involved in substrate recognition and cleavage activity. The size of RNAseP RNA (>350 nucleotides), and the complexity of the substrate recognition, may limit the potential for the use of an RNAseP-like RNA in therapeutics. However, the size of RNAseP is being trimmed down (a molecule of only 290 nucleotides functions reasonably well). In addition, substrate recognition has been simplified by the recent discovery that RNAseP RNA can cleave small RNAs lacking the natural tRNA secondary structure if an additional RNA (containing a "guide" sequence and a sequence element naturally present at the end of all tRNAs) is present as well.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences revealed a common structural design consisting of three stems and loops connected by central loop containing many conserved (invariant from one RNA to the next) nucleotides. The predicted secondary structure for this catalytic RNA reminded the researchers of the head of a hammer consisting of three double helical domains, stems I, II and III and a catalytic core (FIG. 1 and 2a); thus it was named as such. Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate, representing division of the hammerhead domain, along the axes of stems I and II (FIG. 2b) were sufficient to support specific cleavage. The catalytic domain of numerous hammerhead ribozymes have now been studied by both the Uhlenbeck and Symons groups with regard to defining the nucleotides required for specific assembly and catalytic activity and determining the rates of cleavage under various conditions.

Haseloff and Gerlach showed it was possible to divide the domains of the hammerhead ribozyme in a different manner, division of the hammerhead domain along the axes of stems I and III (FIG. 2c). By doing so, they placed most of the required sequences in the strand that didn't get cut (the ribozyme) and only a required UH where H=C, A, U in the strand that did get cut (the substrate). This resulted in a catalytic ribozyme that could be designed to cleave any UH RNA sequence embedded within a longer "substrate recognition" sequence. The specific cleavage of a long mRNA, in a predictable manner using several such hammerhead ribozymes, was reported in 1988. A further development was the division of the catalytic hammerhead domain along the axes of stems III and II (FIG. 2d, Jeffries and Symons, *Nucleic Acids. Res.* 1989, 17, 1371–1377.)

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction (FIG. 3). As with the hammerhead ribozyme, the hairpin catalytic portion contains most of the sequences required for catalytic activity while only a short sequence (GUC in this case) is required in the target. Hampel and Tritz described the folded structure of this RNA as consisting of a single hairpin and coined the term "hairpin" ribozyme (Bruening and colleagues use the term "paperclip" for this ribozyme motif, see, FIG. 3). Continuing experiments suggest an increasing number of similarities between the hairpin and hammerhead ribozymes in respect to both binding of target RNA and mechanism of cleavage. At the same time, the minimal size of the hairpin ribozyme is still 50–60% larger than the minimal hammerhead ribozyme.

Hepatitis Delta Virus (HDV) is a virus whose genome consists of single-stranded RNA. A small region (~80 nucleotides, FIG. 4) in both the genomic RNA, and in the complementary anti-genomic RNA, is sufficient to support self-cleavage. As the most recently discovered ribozyme, HDV's ability to self-cleave has only been studied for a few years, but is interesting because of its connection to a human disease. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently been achieved by Been, but the rules for targeting different substrate RNAs have not yet been determined fully (see, FIG. 4). Been has also succeeded in reducing the size of the HDV ribozyme to ~60 nucleotides.

The Table I lists some of the characteristics of the ribozymes discussed above.

Ribozymes are RNA molecules having an enzymatic activity which is able to repeatedly cleave other separate RNA molecules in a nucleotide base sequence specific manner. It is said that such enzymatic RNA molecules can be targeted to virtually any RNA transcript and efficient cleavage has been achieved in vitro. Kim et al., 84 *Proc. Nat. Acad. of Sci. USA* 8788, 1987; Haseloff and Gerlach, 334 *Nature* 585, 1988; Cech, 260 *JAMA* 3030, 1988; and Jefferies et al., 17 *Nucleic Acid Research* 1371, 1989.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

By "enzymetic RNA molecule" it is meant an RNA molecule which has complementarity in a substrate binding region to a specified mRNA target, and also has an enzymetic activity which is active to specifically cleave that mRNA. That is, the enzymetic RNA molecule is able to intermolecularly cleave mRNA and thereby inactivate a target mRNA molecule. This complementarity functions to allow sufficient hybridization of the enzymetic RNA molecule to the target RNA to allow the cleavage to occur. One hundred percent complementarity is preferred, but complementarity as low as 50–75% may also be useful in this invention. For in vivo treatment, complementarity between 30 and 45 bases is preferred; although lower numbers are also useful.

By "complementary" is meant a nucleotide sequence that can form hydrogen bond(s) with other nucleotide sequence by either traditional Watson-Crick or other non-traditional types (for example Hoogsteen type) of base-paired interactions.

The enzymetic nature of a ribozyme is advantageous over other technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et el., 1992, *Proc. Natl. Aced. Sci. USA*, 89, 7305–7309). Thus, the specificity of action of a ribozyme is greater than that of an antisense oligonucieotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EPA 0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad, Sci, USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention which is complementary to one or more of the target gene RNA regions, and that it have nucleotide sequences within or surrounding that substrate binding site which impart an RNA cleaving activity to the molecule.

Enzymatic nucleic acids act by first binding to a target RNA (or DNA, see Cech U.S. Pat. No. 5,180,818). Such binding occurs through the target binding portion of an enzymatic nucleic acid which is held in close proximity to an enzymatic portion of molecule that acts to cleave the target RNA. Thus, the enzymatic nucleic acid first recognizes and then binds a target RNA through complementary base-pairing, and once bound to the correct site, acts enzymatically to cut the target RNA. Cleavage of such a target RNA will destroy its ability to direct synthesis of an encoded protein. After an enzymatic nucleic acid has bound and cleaved its RNA target it is released from that RNA to search for another target and can repeatedly bind and cleave new targets.

The invention provides a method for producing a class of enzymatic cleaving agents or antisense molecules which exhibit a high degree of specificity for the RNA or DNA of a desired target. The enzymatic nucleic acid or antisense molecule is preferably targeted to a highly conserved sequence region of a target such that specific treatment of a disease or condition can be provided with a single enzymatic nucleic acid. Such, nucleic acid molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead structure) are used for exogenous delivery. The simple structure of these molecules increases the ability of the enzymatic nucleic acid to invade targeted regions of the mRNA structure. Unlike the situation when the hammerhead structure is included within longer transcripts, there are no non-enzymatic nucleic acid flanking sequences to interfere with correct folding of the enzymatic nucleic acid structure or with complementary regions.

Generally, RNA is synthesized and purified by methodologies based on: tetrazole to activate the RNA amidite, $NH_4OH$ to remove the exocyclic amino protecting groups, tetra-n-butylammonium fluoride (TBAF) to remove the 2'-OH alkylsilyl protecting groups, and gel purification and analysis of the deprotected RNA. In particular this applies to, but is not limited to, a certain class of RNA molecules, ribozymes. These may be formed either chemically or using enzymatic methods. Examples of the chemical synthesis, deprotection, purification and analysis procedures are provided by Usman et al., 1987 *J. American Chem. Soc.*, 109, 7845, Scaringe et al. *Nucleic Acids Res.* 1990, 18, 5433–5341, Perreauit et al. *Biochemistry* 1991, 30 4020–4025, and Slim and Gait *Nucleic Acids Res.* 1991, 19, 1183–1188. Odai et al. *FEBS Lett.* 1990, 267, 150–152 describes a reverse phase chromatographic purification of RNA fragments used to form a ribozyme. All the above noted references are all hereby incorporated by reference herein.

The aforementioned chemical synthesis, deprotection, purification and analysis procedures are time consuming (10–15 m coupling times) and may also be affected by inefficient activation of the RNA amidites by tetrazole, time consuming (6–24 h) and incomplete deprotection of the exocyclic amino protecting groups by NH$_4$OH, time consuming (6–24 h), incomplete and difficult to desalt TBAF-catalyzed removal of the alkylsilyl protecting groups, time consuming and low capacity purification of the RNA by gel electrophoresis, and low resolution analysis of the RNA by gel electrophoresis.

Imazawa and Eckstein, 1979 *J. Org. Chem.*, 12, 2039, describe the synthesis of 2'-amino-2'-deoxyribofuranosyl purines. They state that "To protect the 2'-amino function, we selected the trifluoroacetyl group which can easily be removed."

SUMMARY OF THE INVENTION

This invention concerns the chemical synthesis, deprotection, and purification of RNA, enzymatic RNA or modified RNA molecules in greater than milligram quantities with high biological activity. Applicant has determined that the synthesis of enzymatically active RNA in high yield and quantity is dependent upon certain critical steps used during its preparation. Specifically, it is important that the RNA phosphoramidites are coupled efficiently in terms of both yield and time, that correct exocyclic amino protecting groups be used, that the appropriate conditions for the removal of the exocyclic amino protecting groups and the alkylsilyl protecting groups on the 2'-hydroxyl are used, and that the correct work-up and purification procedure of the resulting ribozyme be used.

To obtain a correct synthesis in terms of yield and biological activity of a large RNA molecule (i.e., about 30 to 40 nucleotide bases), the protection of the amino functions of the bases requires either amide or substituted amide protecting groups, which must be, on the one hand, stable enough to survive the conditions of synthesis, and on the other hand, removable at the end of the synthesis. These requirements are met by the amide protecting groups shown in FIG. 6, in particular, benzoyl for adenosine, isobutyryl or benzoyl for cytidine, and isobutyryl for guanosine, which may be removed at the end of the synthesis by incubating the RNA in NH$_3$/EtOH (ethanolic ammonia) for 20 h at 65° C. In the case of the phenoxyacetyl type protecting groups shown in FIG. 6 on guanosine and adenosine and acetyl protecting groups on cytidine, an incubation in ethanolic ammonia for 4 h at 65° C. is used to obtain complete removal of these protecting groups. Removal of the alkylsilyl 2'-hydroxyl protecting groups can be accomplished using a tetrahydrofuran solution of TBAF at room temperature for 8–24 h.

The most quantitative procedure for recovering the fully deprotected RNA molecule is by either ethanol precipitation, or an anion exchange cartridge desalting, as described in Scaringe et al. *Nucleic Acids Res.* 1990, 18, 5433–5341. The purification of the long RNA sequences may be accomplished by a two-step chromatographic procedure in which the molecule is first purified on a reverse phase column with either the trityl group at the 5' position on or off. This purification is accomplished using an acetonitrile gradient with triethylammonium or bicarbonate salts as the aqueous phase. In the case of the trityl on purification, the trityl group may be removed by the addition of an acid and drying of the partially purified RNA molecule. The final purification is carried out on an anion exchange column, using alkali metal perchlorate salt gradients to elute the fully purified RNA molecule as the appropriate metal salts, e.g. Na$^+$, Li$^+$ etc. A final de-salting step on a small reverse-phase cartridge completes the purification procedure. Applicant has found that such a procedure not only fails to adversely affect activity of a ribozyme, but may improve its activity to cleave target RNA molecules.

Applicant has also determined that significant (see Tables 2–4) improvements in the yield of desired full length product (FLP) can be obtained by:

1. Using 5-S-alkyltetrazole at a delivered or effective concentration of 0.25–0.5M or 0.15–0.35M for the activation of the RNA (or analogue) amidite during the coupling step. (By delivered is meant that the actual amount of chemical in the reaction mix is known. This is possible for large scale synthesis since the reaction vessel is of size sufficient to allow such manipulations. The term effective means that available amount of chemical actually provided to the reaction mixture that is able to react with the other reagents present in the mixture. Those skilled in the art will recognize the meaning of these terms from the examples provided herein.) The time for this step is shortened from 10–15 m, vide supra, to 5–10 m. Alkyl, as used herein, refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, NO$_2$ or N(CH$_3$)$_2$, amino, or SH. The term also includes alkenyl groups which are unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, NO$_2$, halogen, N(CH$_3$)$_2$, amino, or SH. The term "alkyl" also includes alkynyl groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, NO$_2$ or N(CH$_3$)$_2$, amino or SH.

Such alkyl groups may also include aryl, alkylaryl, carbocyclic aryl, heterocyclic aryl, amide and ester groups. An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above. Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

2. Using 5-S-alkyltetrazole at an effective, or final, concentration of 0.1-0.35M for the activation of the RNA (or analogue) amidite during the coupling step. The time for this step is shortened from 10-15m, vide supra., to 5-10 m.

3. Using alkylamine (MA, where alkyl is preferably methyl, ethyl, propyl or butyl) or NH₄OH/alkylamine (AMA, with the same preferred alkyl groups as noted for MA) @ 65° C. for 10-15 m to remove the exocyclic amino protecting groups (vs 4-20 h @55°-65° C. using NH₄OH/EtOH or NH₃/EtOH, vide supra). Other alkylamines, e.g. ethylamine, propylamine, butylamine etc. may also be used.

4. Using anhydrous triethylamineohydrogen fluoride (aHF.TEA) @ 65° C. for 0.5-1.5 h to remove the 2'-hydroxyl alkylsilyl protecting group (vs 8-24 h using TBAF, vide supra or TEA.3HF for 24 h (Gasparutto et al. *Nucleic Acids Res.* 1992, 20, 5159-5166). Other alkylamine.HF complexes may also be used, e.g. trimethylamine or diisopropylethylamine.

5. The use of anion-exchange resins to purify and/or analyze the fully deprotected RNA. These resins include, but are not limited to, quartenary or tertiary amino derivatized stationary phases such as silica or polystyrene. Specific examples include Dionex-NA100®, Mono-Q®, Poros-Q®.

Thus, in various aspects, the invention features an improved method for the coupling of RNA phosphoramidites; for the removal of amide or substituted amide protecting groups; and for the removal of 2'-hydroxyl alkylsilyl protecting groups. Such methods enhance the production of RNA or analogs of the type described above (e.g., with substituted 2'-groups), and allow efficient synthesis of large amounts of such RNA. Such RNA may also have enzymatic activity and be purified without loss of that activity. While specific examples are given herein, those in the art will recognize that equivalent chemical reactions can be performed with the alternative chemicals noted above, which can be optimized and selected by routine experimentation.

In another aspect, the invention features an improved method for the purification or analysis of RNA or enzymatic RNA molecules (e.g. 28-70 nucleotides in length) by passing said RNA or enzymatic RNA molecule over an HPLC, e.g., reverse phase and/or an anion exchange chromatography column. The method of purification improves the catalytic activity of enzymatic RNAs over the gel purification method (see FIG. 8).

This invention also features a method for preparation of pure enzymatically active ribozymes (of size between 28 and 70 nucleotide bases) in sodium, potassium or magnesium salt form by a two step purification method. Generally the method is applicable to both synthetically and enzymatically produced ribozymes, and entails use of high performance liquid chromatography (HPLC) techniques on reverse phase columns. Unlike gel purification, HPLC purification as described in this application can be applied to virtually unlimited amounts of purified material. This allows generation of kilogram quantities of ribozymes in each purification batch.

Thus, in another aspect, the invention features a method for purification of an enzymatic RNA molecule of 28-70 nucleotide bases by passing that enzymatic RNA molecule over a high pressure liquid chromatography column.

Surprisingly, applicant has determined that enzymatically active ribozymes can be purified in the desired salt form by the described HPLC or anion exchange methodology.

In preferred embodiments, the method includes passing the enzymatically active RNA molecule over a reverse phase HPLC column; the enzymatically active RNA molecule is produced in a synthetic chemical method and not by an enzymatic process; and the enzymatic RNA molecule contains a 5'-DMT group, and the 5'-DMT-containing enzymatically active RNA molecule is passed over a reverse phase HPLC column to separate it from other RNA molecules.

In a related aspect, the invention features pure ribozyme in a Na⁺, K⁺, or Mg²⁺ salt form. By "pure" is meant that the ribozyme is preferably provided free of other contaminants, and is at least 85% in the desired salt form.

Thus, the purification of long RNA molecules may be accomplished using anion exchange chromatography, particularly in conjunction with alkali perchlorate salts. This system may be used to purify very long RNA molecules. In particular, it is advantageous to use a Dionex NucleoPak 100© or a Pharmacia Mono Q® anion exchange column for the purification of RNA by the anion exchange method. This anion exchange purification may be used following a reverse-phase purification or prior to reverse phase purification. This method results in the formation of a sodium salt of the ribozyme during the chromatography. Replacement of the sodium alkali earth salt by other metal salts, e.g., lithium, magnesium or calcium perchlorate, yields the corresponding salt of the RNA molecule during the purification.

In the case of the 2-step purification procedure, in which the first step is a reverse phase purification followed by an anion exchange step, the reverse phase purification is best accomplished using polymeric, e.g. polystyrene based, reverse-phase media, using either a 5'-trityl-on or 5'-trityl-off method. Either molecule may be recovered using this reverse-phase method, and then, once detritylated, the two fractions may be pooled and then submitted to an anion exchange purification step as described above.

The method includes passing the enzymatically active RNA molecule over a reverse phase HPLC column; the enzymatically active RNA molecule is produced in a synthetic chemical method and not by an enzymatic process; and the enzymatic RNA molecule is partially blocked, and the partially blocked enzymatically active RNA molecule is passed over a reverse phase HPLC column to separate it from other RNA molecules.

In more preferred embodiments, the enzymatically active RNA molecule, after passage over the reverse phase HPLC column, is deprotected and passed over a second reverse phase HPLC column (which may be the same as the reverse phase HPLC column), to remove the enzymatic RNA molecule from other components. In addition, the column is a silica or organic polymer-based C4, C8 or C18 column having a porosity of at least 125 Å, preferably 300 Å, and a particle size of at least 2 μm, preferably 5 μm.

Other features and advantages of the invention will be apparent from the following description of the preferred embodiments thereof, and from the claims.

DESCRIPTION OF THE PREFERRED EMBODIMENTS

The drawings will first briefly be described.

Figure 3:
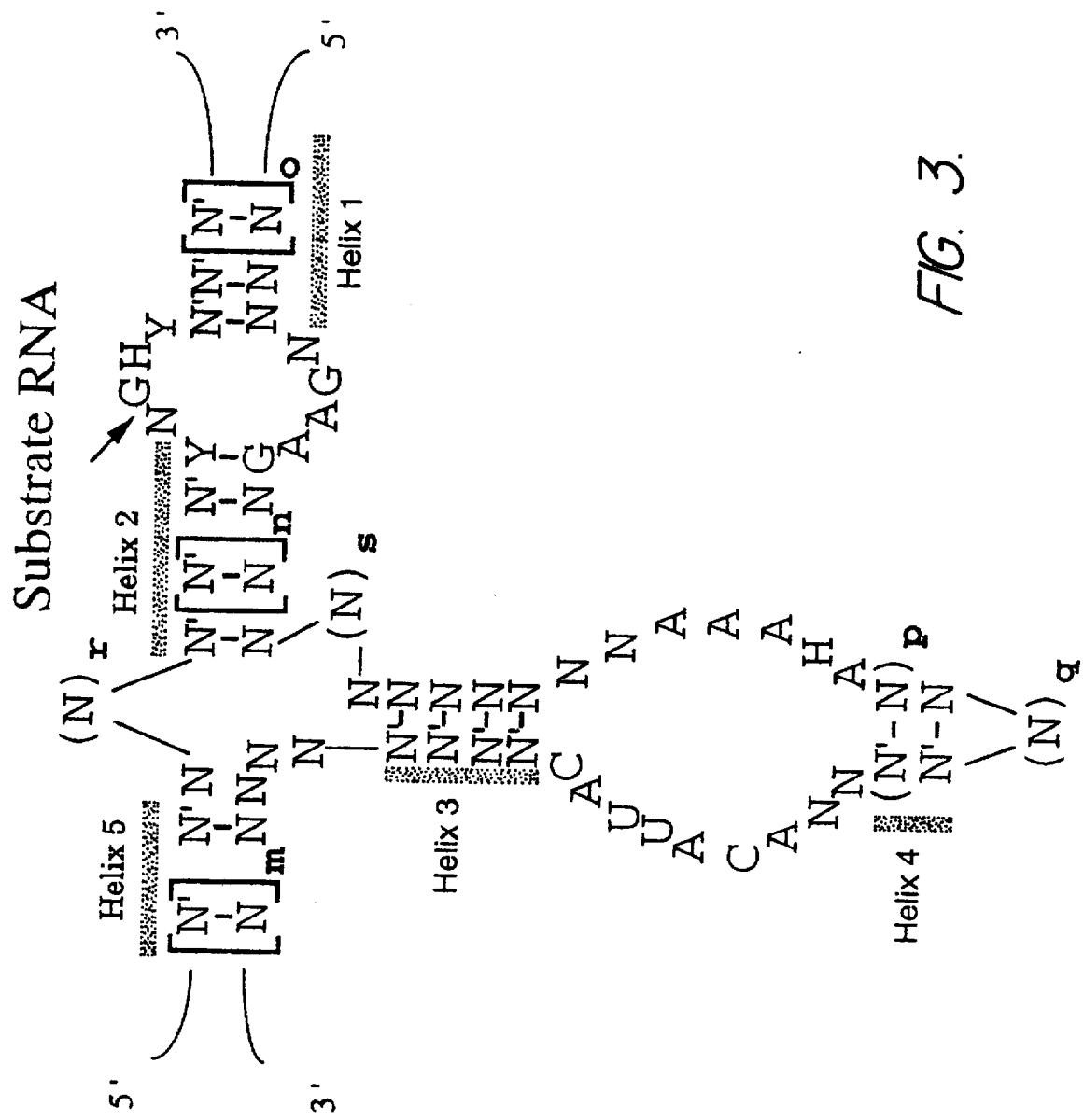

FIG. 3 is a diagrammatic representation of the general structure of a hairpin ribozyme (SEQ ID Nos. 3 and 4). Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases. "____" refers to a chemical bond.

Figure 4A:
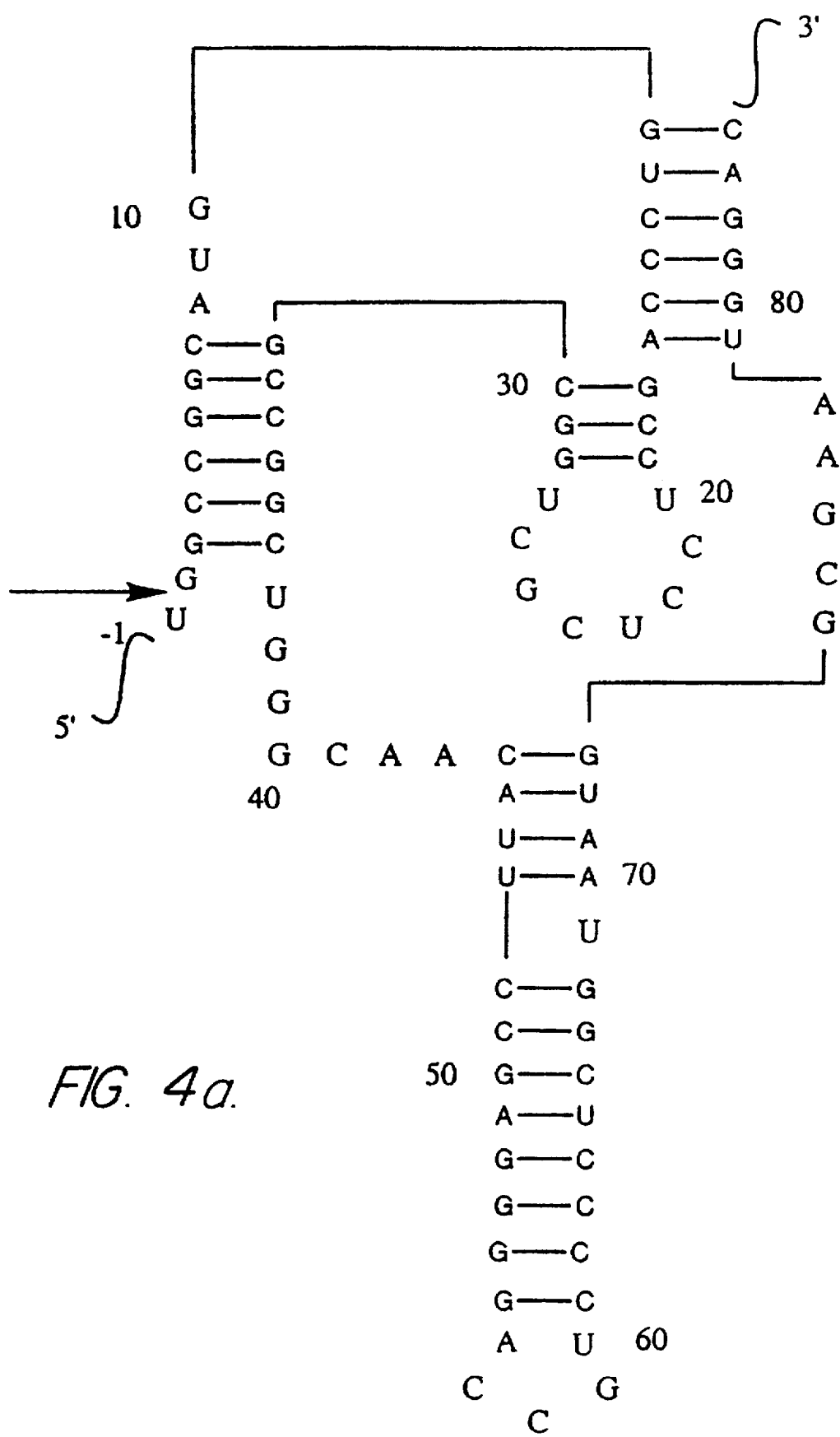

FIG. 4A is a representation of the general structure of the hepatitis delta virus ribozyme domain (SEQ ID No. 5) known in the art.

Figure 4B:
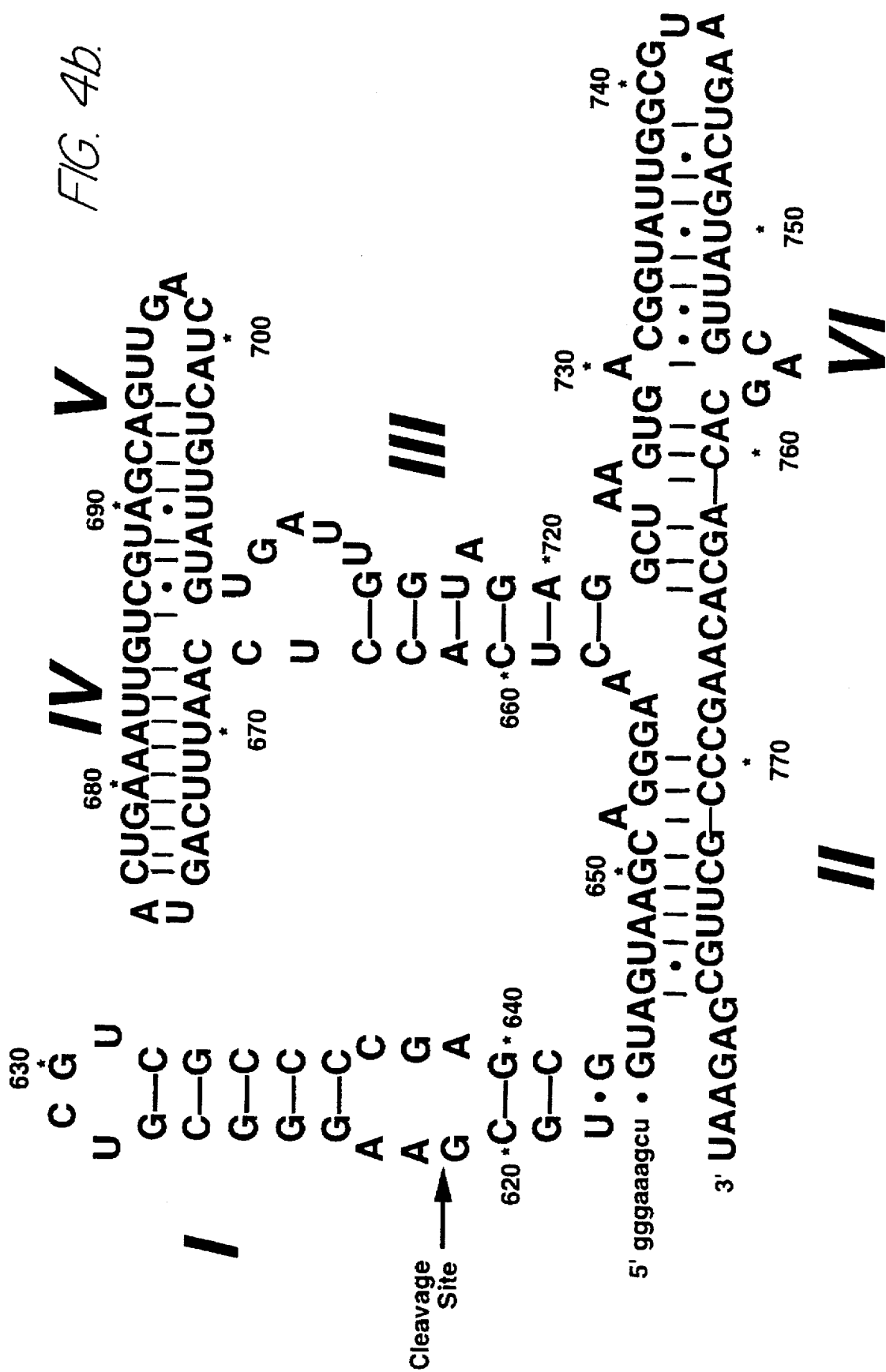

FIG. 4B is a representation of the general structure of the self-cleaving VS RNA ribozyme domain (Seq. ID NO.6).

Figure 5:
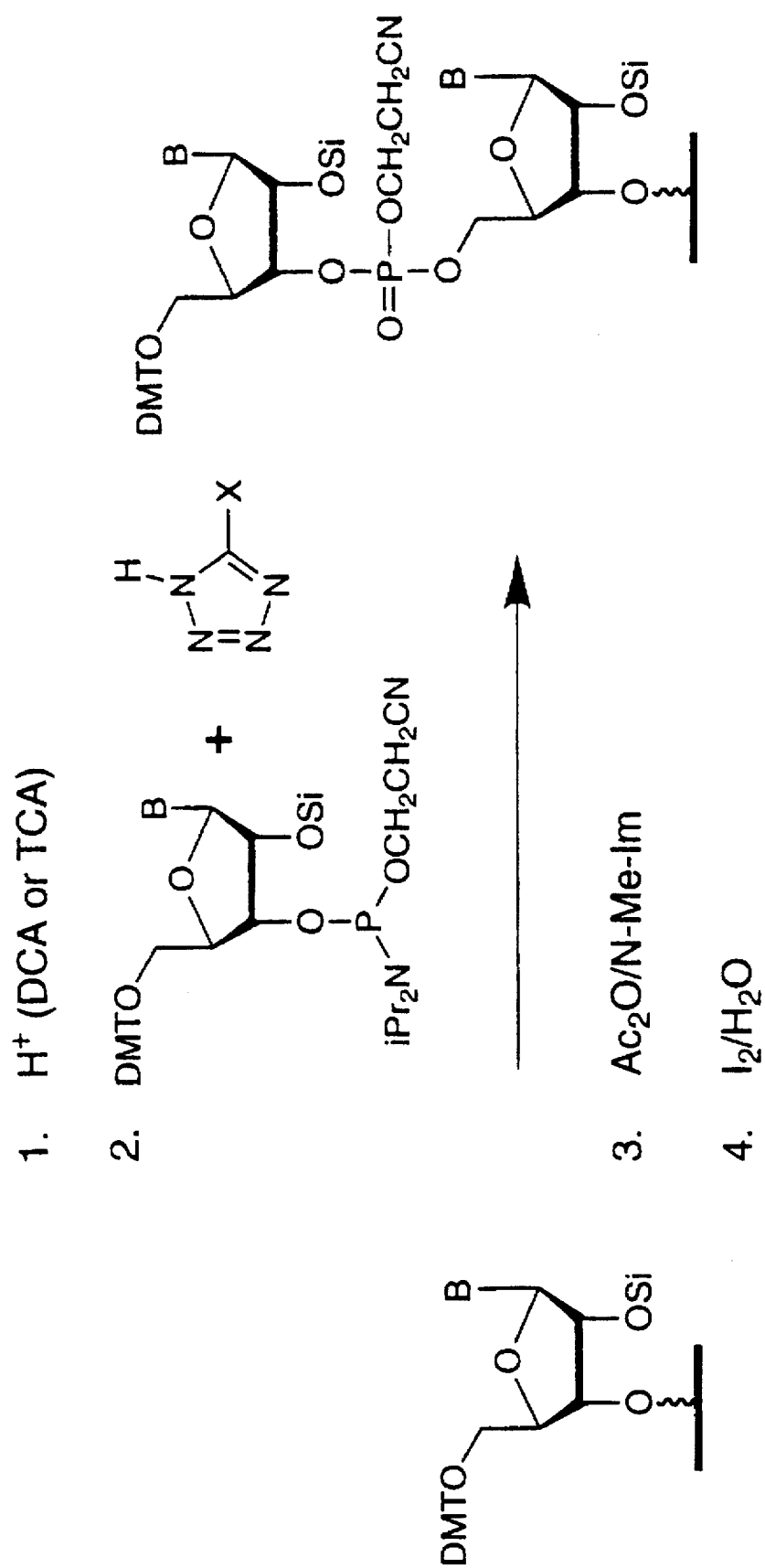

FIG. 5 is a diagrammatic representation of the solid-phase synthesis of RNA.

Figure 6:
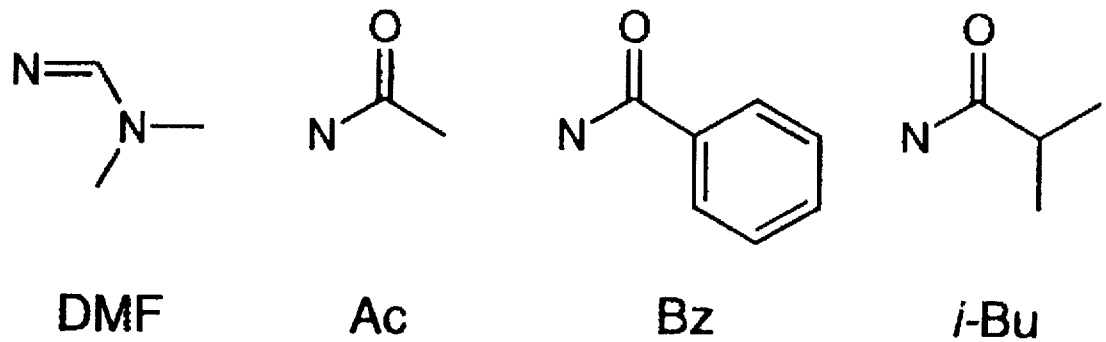
Figure 6:
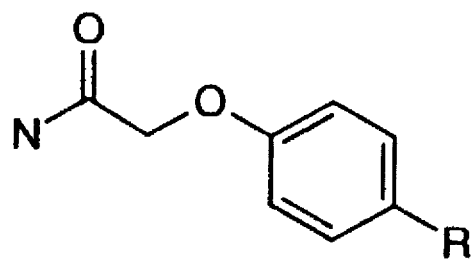

FIG. 6 is a diagrammatic representation of exocyclic amino protecting groups for nucleic acid synthesis.

Figure 7:
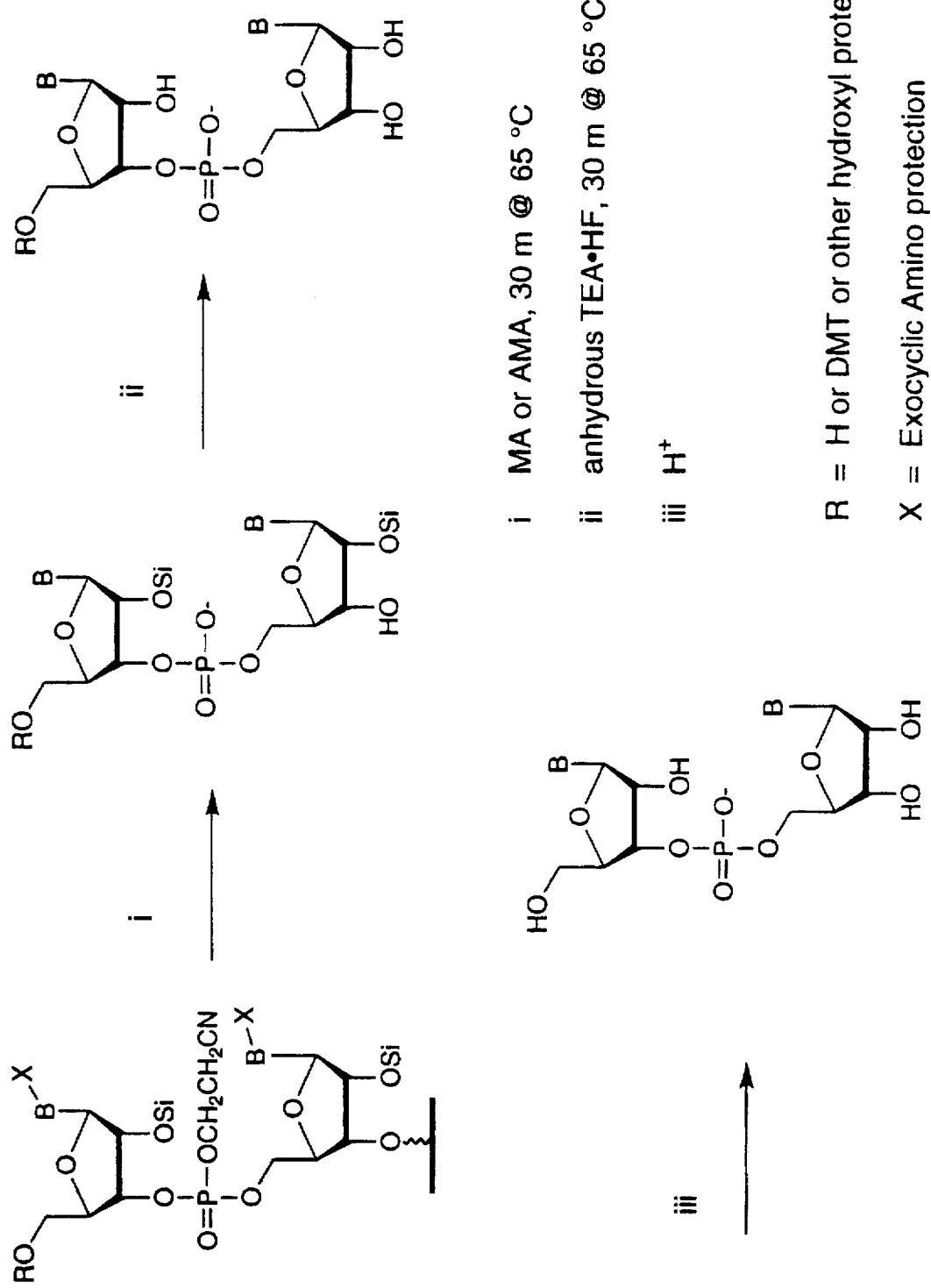

FIG. 7 is a diagrammatic representation of the deprotection of RNA.

Figure 8:
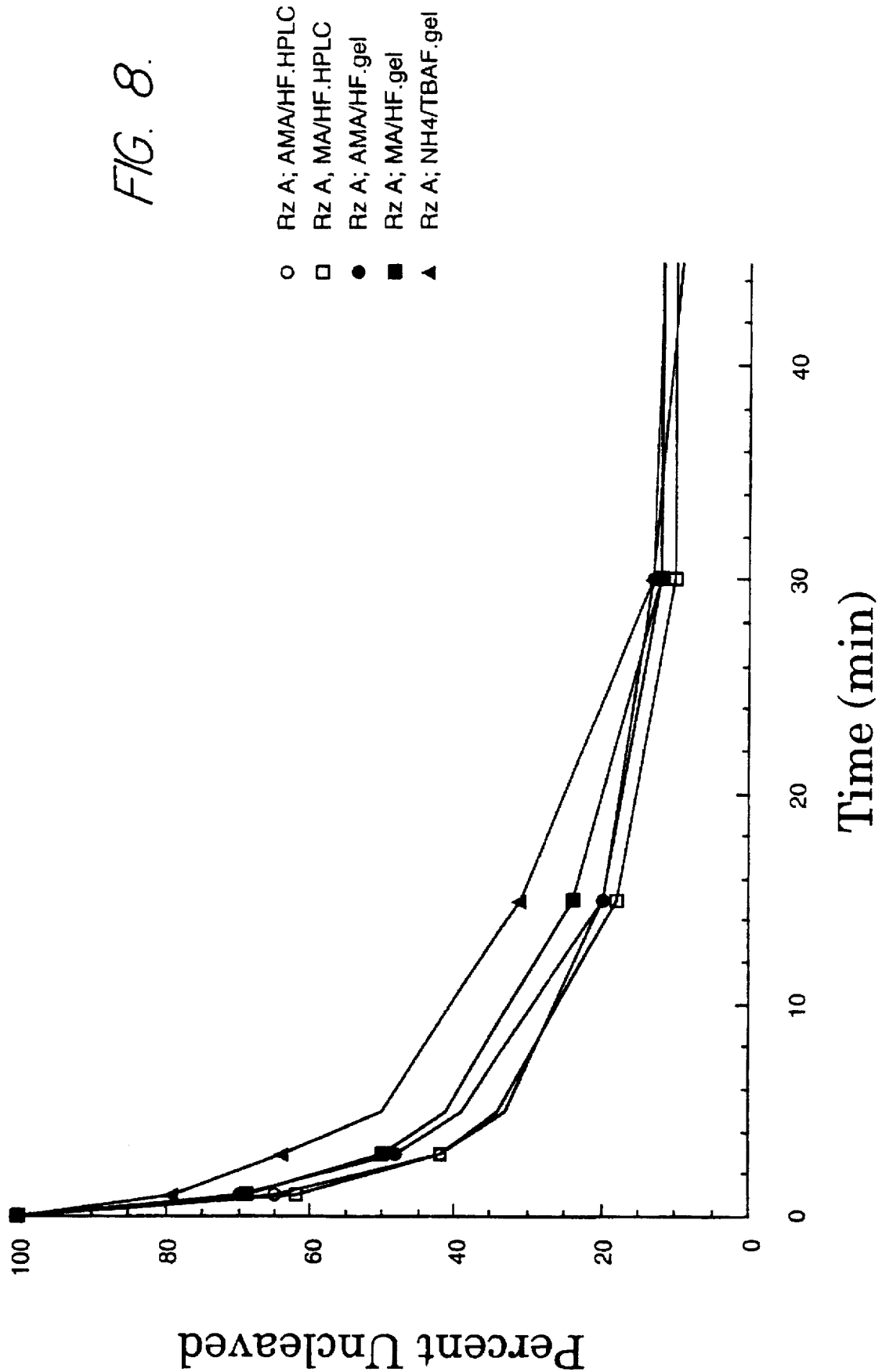

FIG. 8 is a graphical representation of the cleavage of an RNA substrate by ribozymes synthesized, deprotected and purified using the improved methods described herein.

Figure 9:
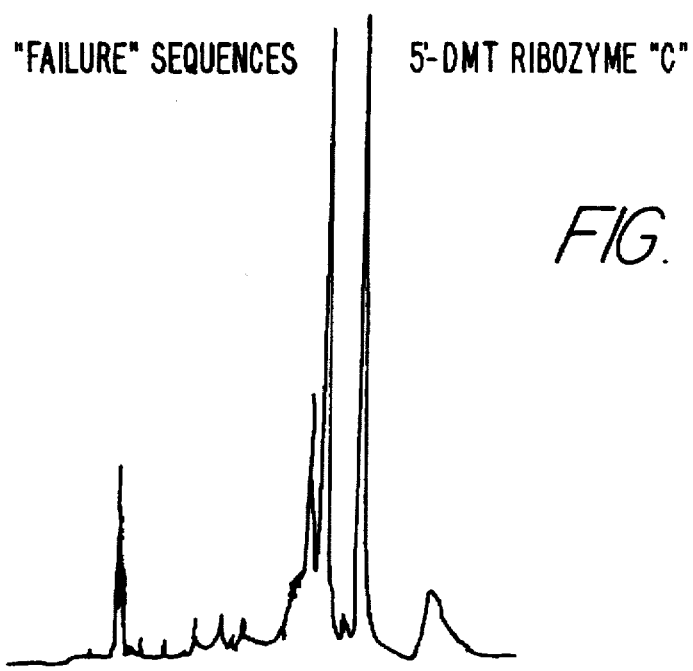
Figure 10:
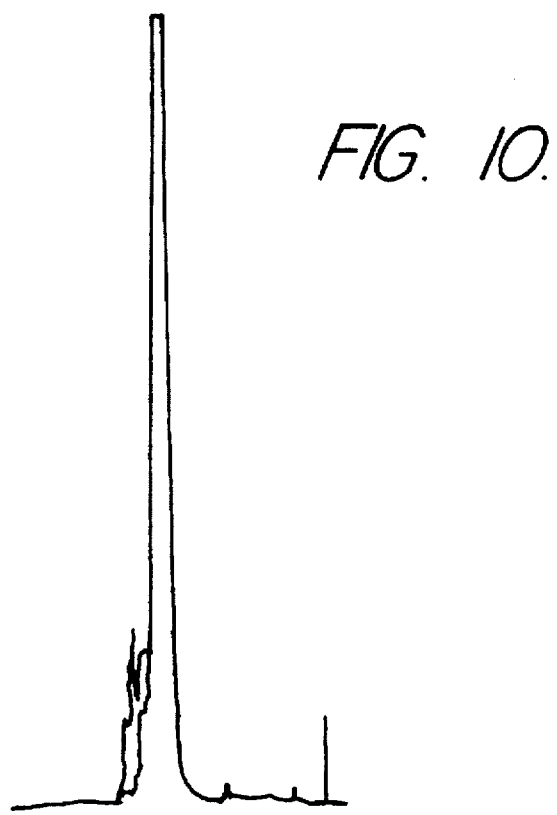

FIGS. 9 and 10 are copies of HPLC results showing purification of ribozyme from failure sequences (FIG. 9) and other contaminants (FIG. 10).

Figure 11:
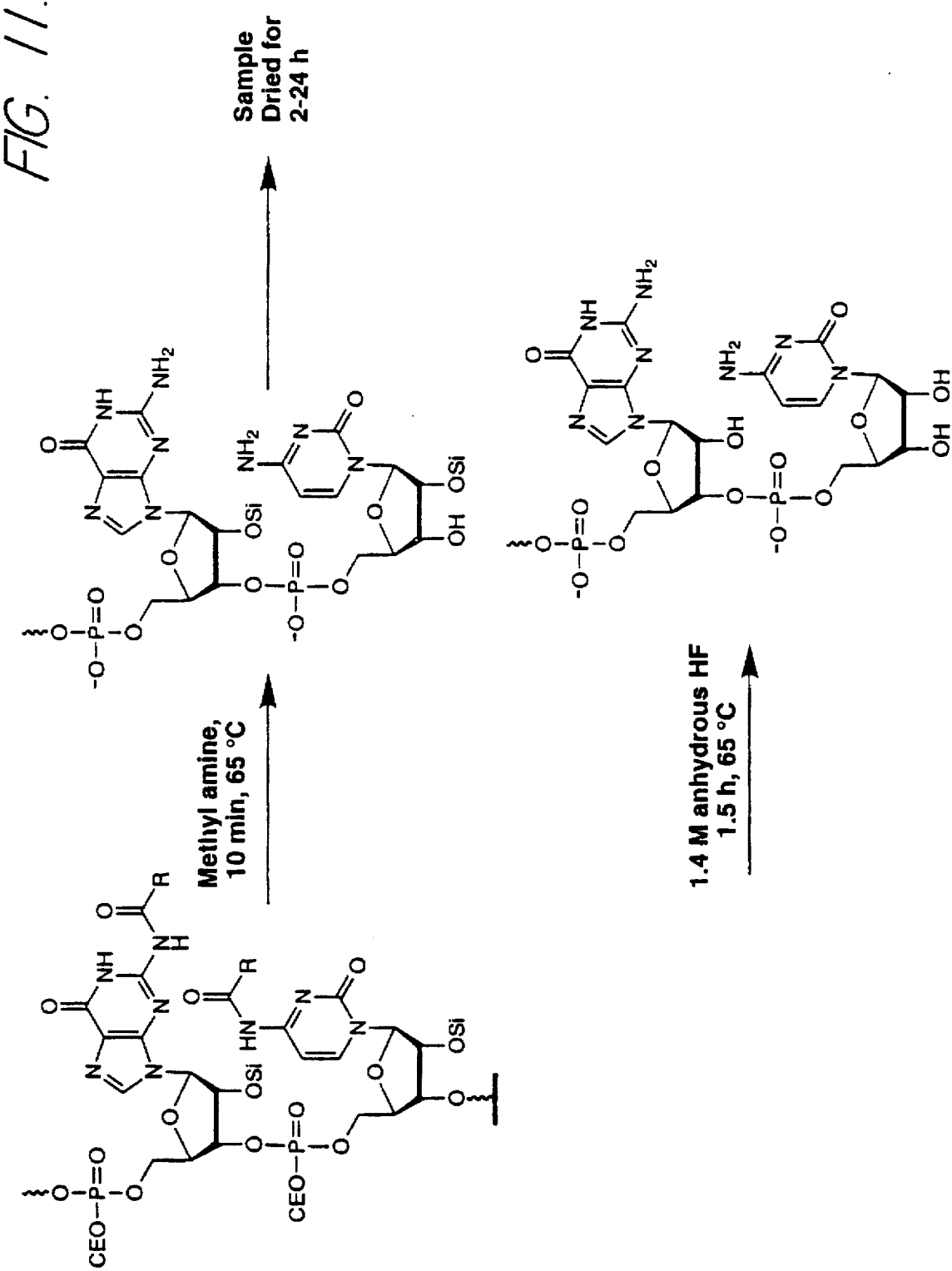

FIG. 11 is a schematic representation of a two pot deprotection protocol. Base deprotection is carried out with aqueous methyl amine at 65° C. for 10 min. The sample is dried in a speed-vac for 2–24 hours depending on the scale of RNA synthesis. Silyl protecting group at the 2'-hydroxyl position is removed by treating the sample with 1.4M anhydrous HF at 65° C. for 1.5 hours.

Figure 12:
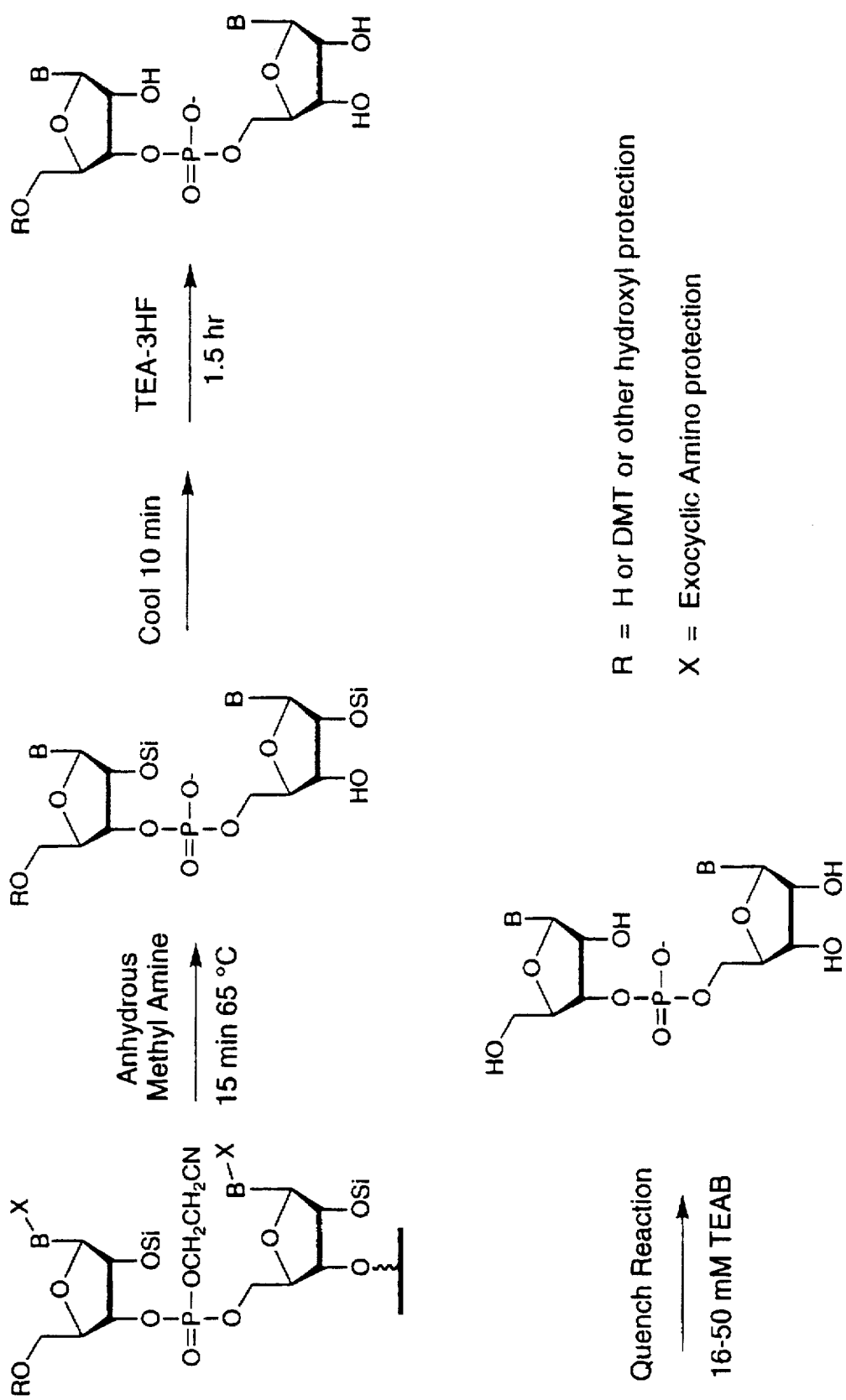

FIG. 12 is a schematic representation of a one pot deprotection of RNA synthesized using RNA phosphoramidite chemistry. Anhydrous methyl amine is used to deprotect bases at 65° C. for 15 min. The sample is allowed to cool for 10 min before adding TEA.3HF reagent, to the same pot, to remove protecting groups at the 2'-hydroxyl position. The deprotection is carried out for 1.5 hours.

Figure 13A:
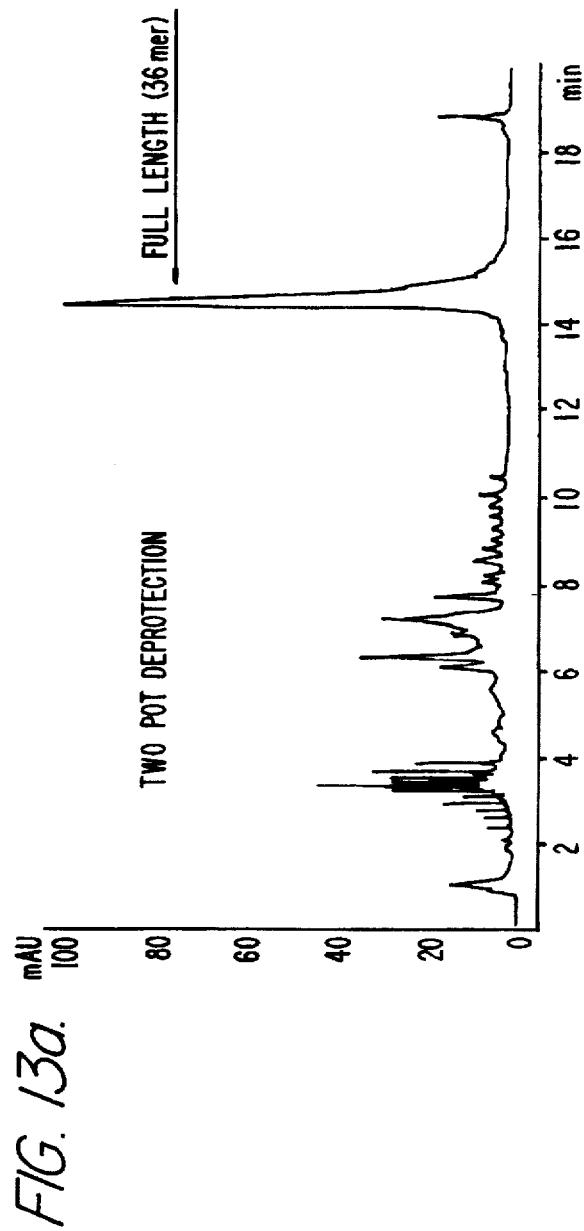
Figure 13B:
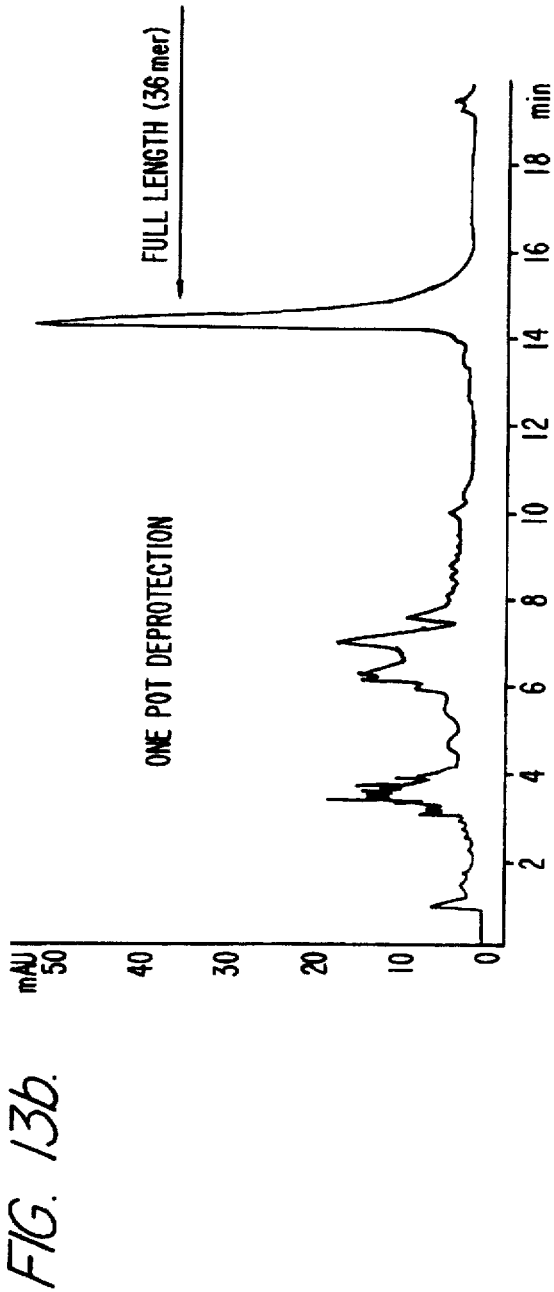

FIG. 13 is a HPLC profile of a 36 nt long ribozyme, targeted to site A. The RNA is deprotected using either the two pot or the one pot deprotection protocol. The peaks corresponding to full-length RNA is indicated.

Figure 14:
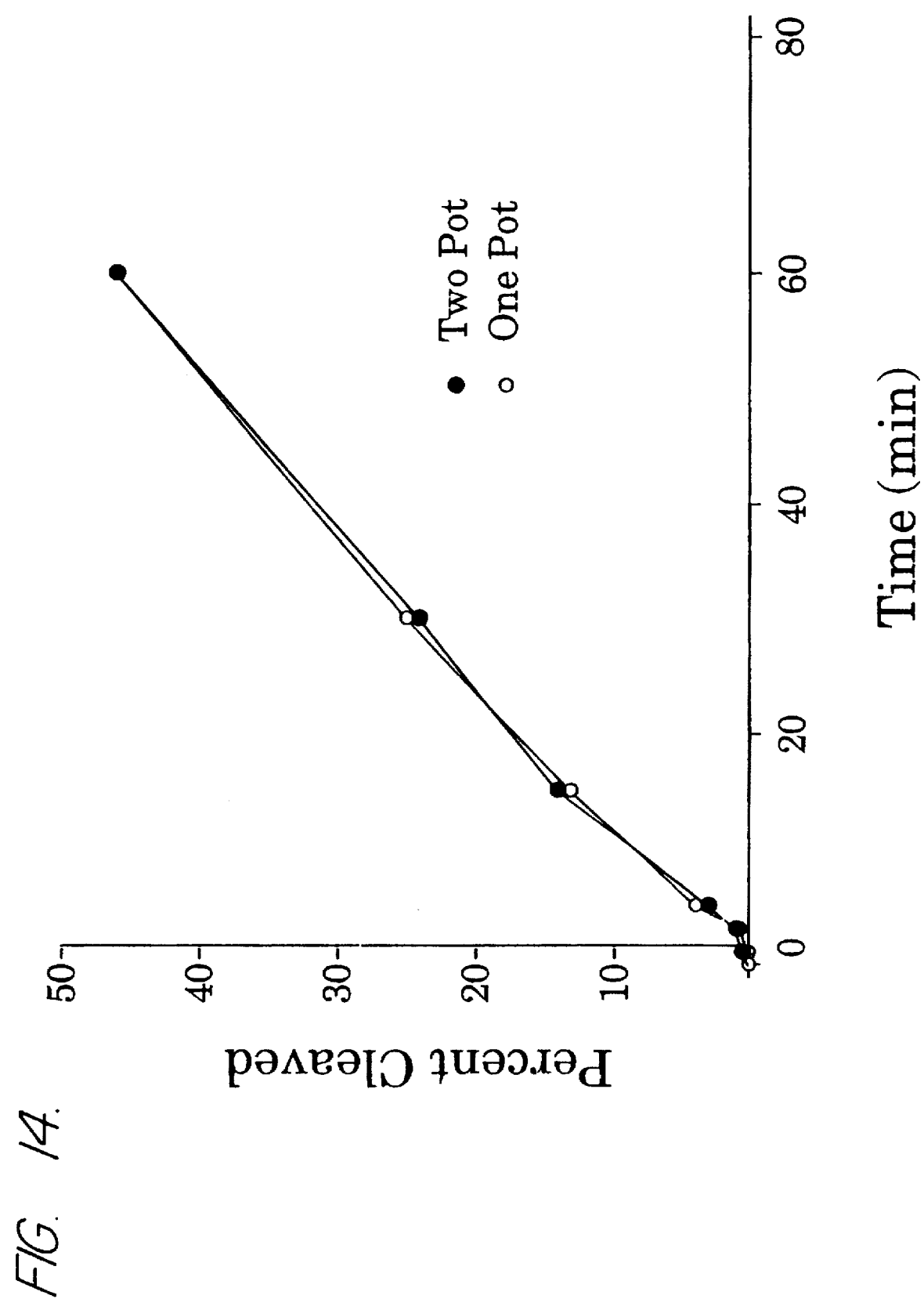

FIG. 14 is a graph comparing RNA cleavage activity of ribozymes deprotected by two pot vs one pot deprotection protocols.

Figure 15:
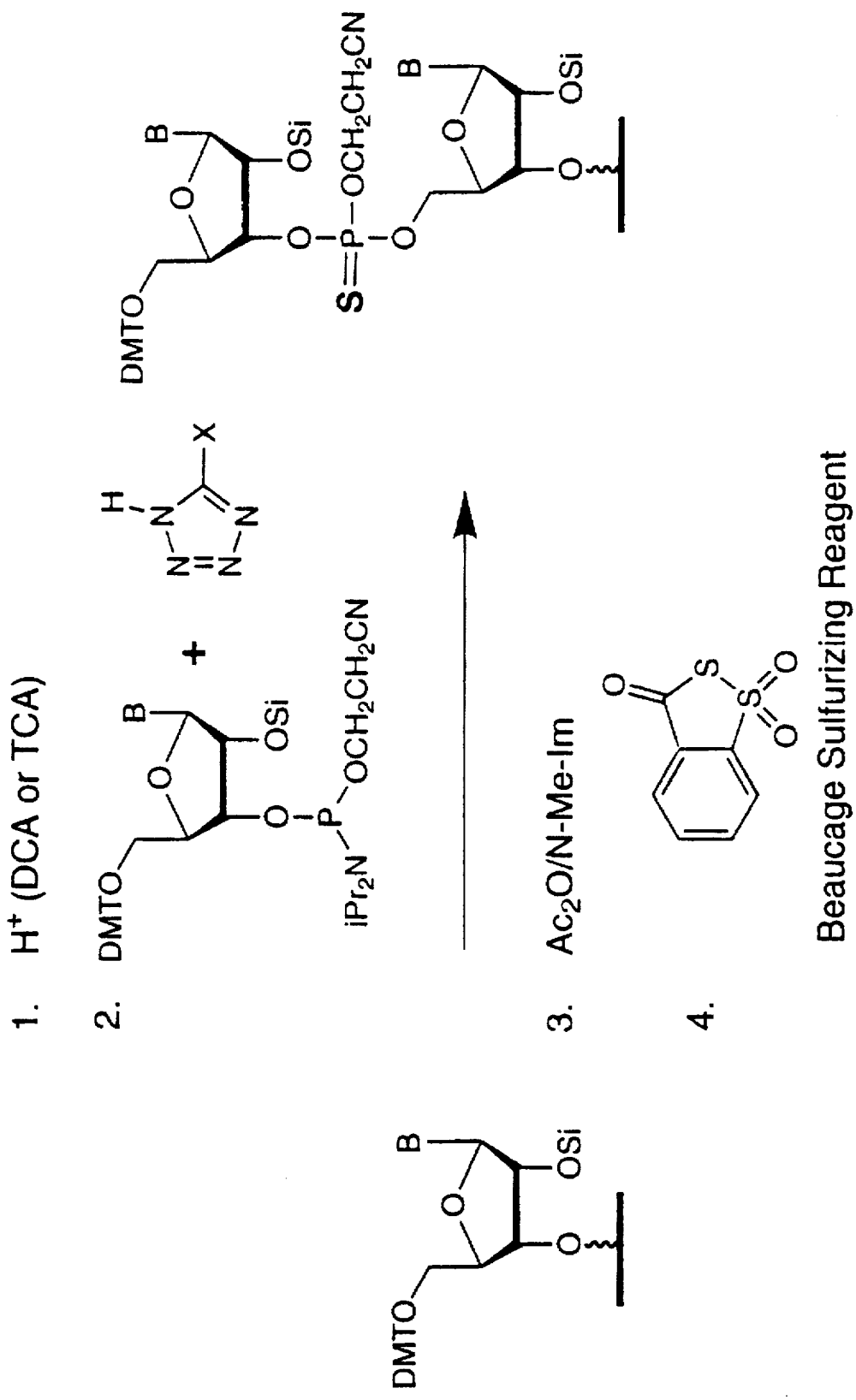

FIG. 15 is a schematic representation of an improved method of synthesizing RNA containing phosphorothioate linkages.

Figure 16:
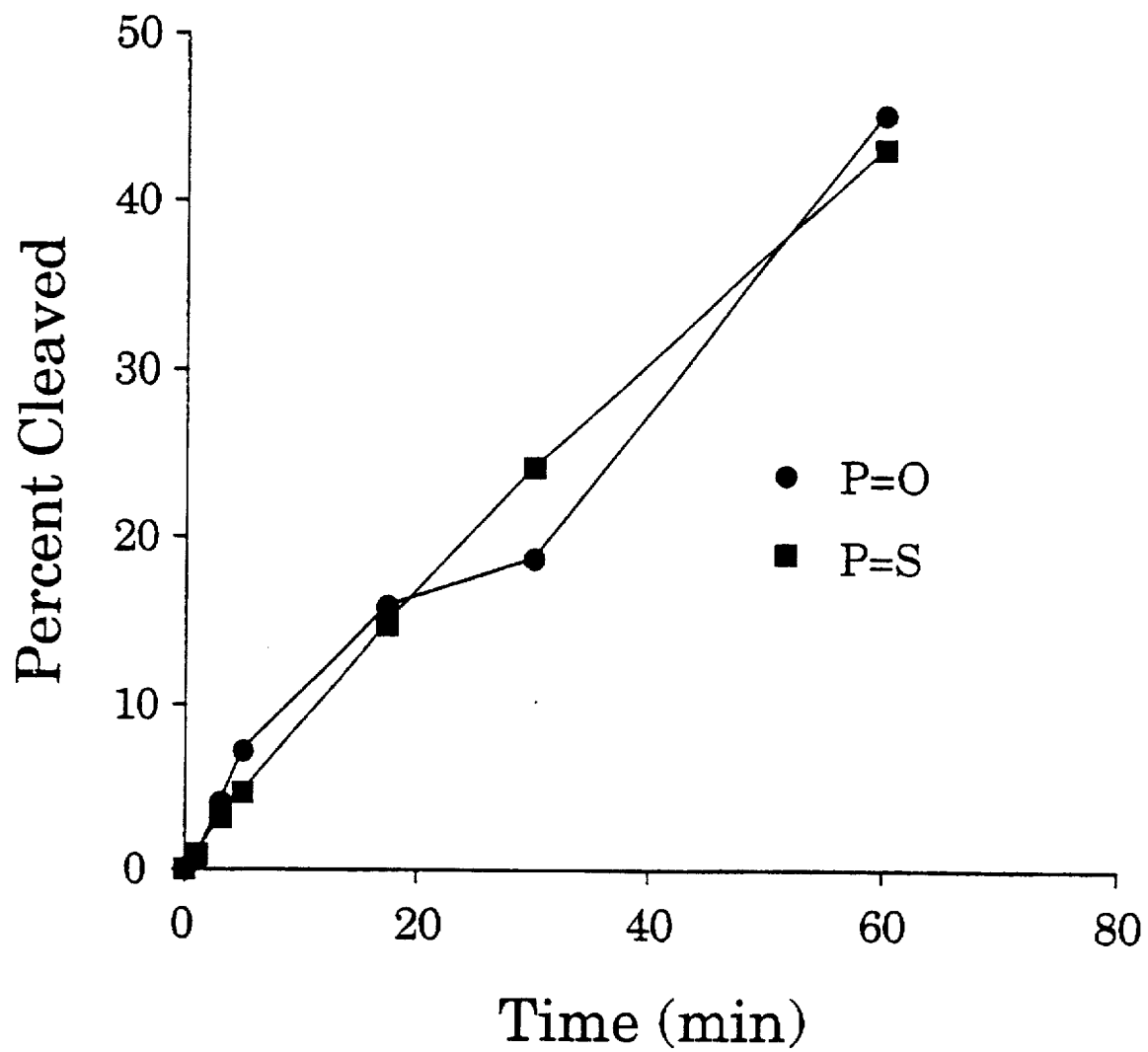

FIG. 16 shows RNA cleavage reaction catalyzed by ribozymes containing phosphorothioate linkages. Hammerhead ribozyme targeted to site A is synthesized such that 4 nts at the 5' end contain phosphorothioate linkages. P=O refers to ribozyme without phosphorothioate linkages. P=S refers to ribozyme with phosphorothioate linkages.

Figure 17:
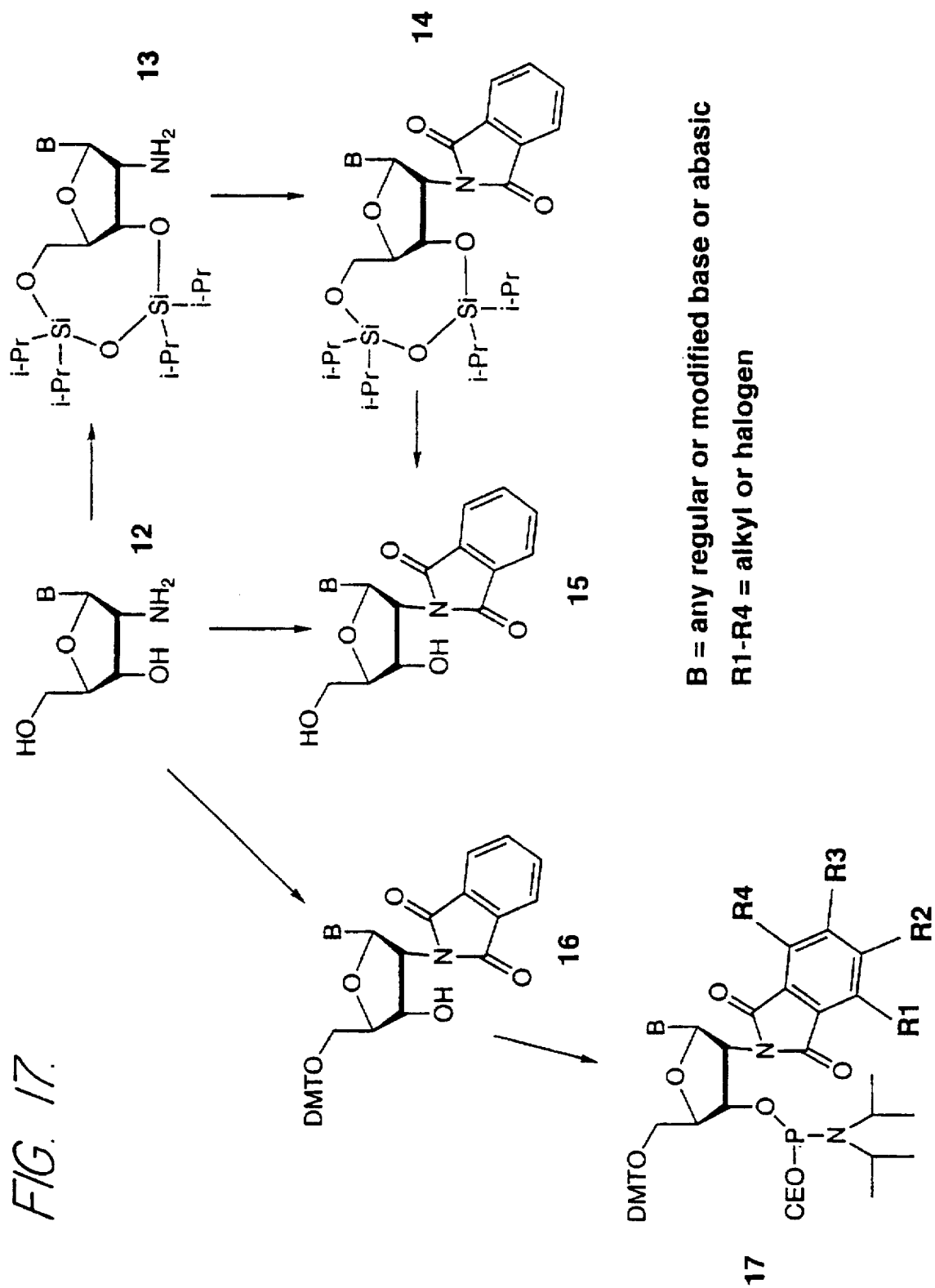

FIG. 17 is a schematic representation of synthesis of 2'-N-phtalimido-nucleoside phosphoramidite.

EXAMPLES

The following are non-limiting examples showing the synthesis of RNA-containing nucleic acids and the testing of the enzymatic activity of these molecules when they are catalytic RNAs.

Activation

The synthesis of RNA molecules may be accomplished chemically or enzymatically. In the case of chemical synthesis the use of tetrazole as an activator of RNA phosphoramidites is known (Usman et al. *J. Am. Chem. Soc.* 1987, 109, 7845–7854). In this, and subsequent reports, a 0.5M solution of tetrazole is allowed to react with the RNA phosphoramidite and couple with the polymer bound 5'-hydroxyl group for 10 m. Applicant has determined that using 0.25–0.5M solutions of 5-S-alkyltetrazoles for only 5 min gives equivalent or better results. The following exemplifies the procedure.

Example 1

Synthesis of RNA and Ribozymes Using 5-S-Alkyltetrazoles as Activating Agent

The method of synthesis used follows the general procedure for RNA synthesis as described in Usman et al., 1987 supra and in Scaringe et al., *Nucleic Acids Res.* 1990, 18, 5433–5441 and makes use of common nucleic acid protecting and coupling groups, such as dimethoxytrityl at the 5'-end, and phosphoramidites at the 3'-end. The major difference used, was the activating agent, 5-S-ethyl or -methyltetrazole @ 0.25M concentration for 5 min.

All small scale syntheses were conducted on a 394 (ABI) synthesizer using a modified 2.5 µmol scale protocol with a reduced 5 min coupling step for alkylsilyl protected RNA and 2.5 m coupling step for 2'-O-methylated RNA. A 6.5-fold excess (162.5 µL of 0.1M=32.5 µmol) of phosphoramidite and a 40-fold excess of S-ethyl tetrazole (400 µL of 0.25M=100 µmol) relative to polymer-bound 5'-hydroxyl was used in each coupling cycle. Average coupling yields on the 394, determined by colorimetric quantitation of the trityl fractions, was 97.5–99%. Other oligonucleotide synthesis reagents for the 394: Detritylation solution was 2% TCA in methylene chloride; capping was performed with 16% N-Methyl imidazole in THF and 10% acetic anhydride/10% 2,6-lutidine in THF; oxidation solution was 16.9 mM $I_2$, 49 mM pyridine, 9% water in THF. Fisher Synthesis Grade acetonitrile was used directly from the reagent bottle. S-Ethyl tetrazole solution (0.25M in acetonitrile) was made up from the solid obtained from Applied Biosystems.

All large scale syntheses were conducted on a modified (eight amidite port capacity) 390Z (ABI) synthesizer using a 25 µmol scale protocol with a 5–15 min coupling step for alkylsilyl protected RNA and 7.5 m coupling step for 2'-O-methylated RNA. A six-fold excess (1.5mL of 0.1M= 150 µmol) of phosphoramidite and a forty-five-fold excess of S-ethyl tetrazole (4.5 mL of 0.25M=1125 µmol) relative to polymer-bound 5'-hydroxyl was used in each coupling cycle. Average coupling yields on the 390Z, determined by colorimetric quantitation of the trityl fractions, was 95.0–96.7%. Oligonucleotide synthesis reagents for the 390Z: Detritylation solution was 2% DCA in methylene chloride; capping was performed with 16% N-Methyl imidazole in THF and 10% acetic anhydride/10% 2,6-lutidine in THF; oxidation solution was 16.9 mM $I_2$, 49 mM pyridine, 9% water in THF. Fisher Synthesis Grade acetonitrile was used directly from the reagent bottle. S-Ethyl tetrazole solution (0.25–0.5M in acetonitrile) was made up from the solid obtained from Applied Biosystems.

Table 1 is a summary of the results obtained using the improvements outlined in this application for the large-scale synthesis of RNA and modified RNAs.

Deprotection

The first step of the deprotection of RNA molecules may be accomplished by removal of the exocyclic amino protecting groups with either $NH_4OH/EtOH$:3/1 (Usman et al. *J. Am. Chem. Soc.* 1987, 109, 7845–7854) or $NH_3$/EtOH (Scaringe et al. *Nucleic Acids Res.* 1990, 18, 5433–5341) for ~20 h @ 55°–65° C. Applicant has determined that the use of methylamine or $NH_4OH$/methylamine for 10–15 min @ 55°–65° C. gives equivalent or better results. The following exemplifies the procedure.

Example 2

RNA and Ribozyme Deprotection of Exocyclic Amino Protecting Groups Using Methylamine (MA) or $NH_4OH$/Methylamine (AMA)

The polymer-bound oligonucleotide, either trityl-on or off, was suspended in a solution of methylamine (MA) or $NH_4OH$/methylamine (AMA) @ 55°–65° C. for 5–15 min to remove the exocyclic amino protecting groups. The polymer-bound oligoribonucleotide was transferred from the synthesis column to a 4 mL glass screw top vial. $NH_4OH$ and aqueous methylamine were pre-mixed in equal volumes. 4 mL of the resulting reagent was added to the vial, equilibrated for 5 m at RT and then heated at 55° or 65° C. for 5–15 min. After cooling to –20° C., the supernatant was removed from the polymer support. The support was washed with 1.0 mL of EtOH:MeCN:$H_2O$/3:1:1, vortexed and the supernatant was then added to the first supernatant. The combined supernatants, containing the oligoribonucleotide, were dried to a white powder. The same procedure was followed for the aqueous methylamine reagent.

Table III is a summary of the results obtained using the improvements outlined in this application for base deprotection.

The second step of the deprotection of RNA molecules may be accomplished by removal of the 2'-hydroxyl alkylsilyl protecting group using TBAF for 8–24 h (Usman et al. *J. Am. Chem. Soc.* 1987, 109, 7845–7854). Applicant has determined that the use of anhydrous TEA.HF in N-methylpyrrolidine (NMP) for 0.5–1.5 h @ 55°–65° C. gives equivalent or better results. The following exemplifies this procedure.

Example 3

RNA and Ribozyme Deprotection of 2'-Hydroxyl Alkylsilyl Protecting Groups Using Anhydrous TEA.HF To remove the alkylsilyl protecting groups, the ammonia-deprotected oligoribonucleotide was resuspended in 250 µL of 1.4M anhydrous HF solution (1.5 mL N-methylpyrrolidine, 750 µL TEA and 1.0 mL TEA.3HF) and heated to 65° C. for 1.5 h. 9 mL of 50 mM TEAB was added to quench the reaction. The resulting solution was loaded onto a Qiagen 500® anion exchange cartridge (Qiagen Inc.) prewashed with 10 mL of 50 mM TEAB. After washing the cartridge with 10 mL of 50 mM TEAB, the RNA was eluted with 10 mL of 2M TEAB and dried down to a white powder.

Table IV is a summary of the results obtained using the improvements outlined in this application for alkylsilyl deprotection.

RNA and Ribozyme Purification

The method of this invention generally features HPLC purification of ribozymes. An example of such purification is provided below in which a synthetic ribozyme produced on a solid phase is blocked. This material is then released from the solid phase by a treatment with methanolic ammonia, subsequently treated with tetrabutylammonium fluoride, and purified on reverse phase HPLC to remove partially blocked ribozyme from "failure" sequences (FIG. 9). Such "failure" sequences are RNA molecules which have a nucleotide base sequence shorter to that of the desired enzymatic RNA molecule by one or more of the desired bases in a random manner, and possess free terminal 5'-hydroxyl group. This terminal 5'-hydroxyl in a ribozyme with the correct sequence is still blocked by lipophilic dimethoxytrityl group. After such partially blocked enzymatic RNA is purified, it is deblocked by a standard procedure, and passed over the same or a similar HPLC reverse phase column to remove other contaminating components, such as other RNA molecules or nucleotides or other molecules produced in the deblocking and synthetic procedures (FIG. 10). The resulting molecule is the native enzymatically active ribozyme in a highly purified form.

Below are provided examples of such a method. These examples can be readily, scaled up to allow production and purification of gram or even kilogram quantities of ribozymes.

Example 4

HPLC Purification, Reverse-Phase

In this example solid phase phosphoramidite chemistry was employed for synthesis of a ribozyme. Monomers used were 2'-t-butyl-dimethylsilyl cyanoethylphosphoramidites of uridine, N-benzoyl-cytosine, N-phenoxyacetyl adenosine, and guanosine (Glen Research, Sterling, Va.).

Solid phase synthesis was carried out on either an ABI 394 or 380B DNA/RNA synthesizer using the standard protocol provided with each machine. The only exception was that the coupling step was increased from 10 to 12 minutes. The phosphoramidite concentration was 0.1M.

Synthesis was done on a 1 µmol scale using a 1 µmol RNA reaction column (Glen Research). The average coupling efficiencies were between 97% and 98% for the 394 model and between 97% and 99% for the 380B model, as determined by a calorimetric measurement of the released trityl cation. The final 5'-DMT group was not removed.

After synthesis, the ribozymes were cleaved from the CPG support, and the base and phosphotriester moieties were deprotected in a sterile vial by incubation in dry ethanolic ammonia (2 mL) at 55° C. for 16 hours. The reaction mixture was cooled on dry ice. Later, the cold liquid was transferred into a sterile screw cap vial and lyophilized.

To remove the 2'-t-butyldimethylsilyl groups from the ribozyme the obtained residue was suspended in 1M tetra-n-butylammonium fluoride in dry THF (TBAF), using a 20-fold excess of the reagent for every silyl group, for 16 hours at ambient temperature. The reaction was quenched by adding an equal volume of a sterile 1M triethylamine acetate, pH 6.5. The sample was cooled and concentrated on a SpeedVac to half of the initial volume.

The ribozymes were purified in two steps by HPLC on a C4 300 Å 5 µm DeltaPak column in an acetonitrile gradient.

The first step, or "trityl on" step, was a separation of 5'-DMT-protected ribozyme(s) from failure sequences lacking a 5'-DMT group. Solvents used for this step were: A (0.1M triethylammonium acetate, pH 6.8) and B (acetonitrile). The elution profile was: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step was a purification of a completely deprotected, i.e. following the removal of the 5'-DMT group, ribozyme by a treatment with 2% trifluoroacetic acid or 80% acetic acid on a C4 300 Å 5 µm DeltaPak column in an acetonitrile gradient. Solvents used for this second step were: A (0.1M Triethylammonium acetate, pH 6.8) and B (80% acetonitrile, 0.1M triethylammonium acetate, pH 6.8). The elution profile was: 5% B for 5 minutes, a linear gradient of 5% B to 15% B over 60 minutes, 15% B for 10 minutes, and a linear gradient of 15% B to 0% B over 10 minutes.

The fraction containing ribozyme, which is in the triethylammonium salt form, was cooled and lyophilized on a SpeedVac. Solid residue was dissolved in a minimal amount of ethanol and ribozyme in sodium salt form was precipitated by addition of sodium perchlorate in acetone. ($K^+$ or $Mg^{2+}$ salts can be produced in an equivalent manner.) The ribozyme was collected by centrifugation, washed three times with acetone, and lyophilized.

Example 5

HPLC Purification, Anion Exchange column

For a small scale synthesis, the crude material was diluted to 5 mL with diethylpyrocarbonate treated water. The sample was injected onto either a Pharmacia Mono Q® 16/10 or Dionex NucleoPac® column with 100% buffer A (10 mM $NaClO_4$). A gradient from 180–210 mM $NaClO_4$ at a rate of 0.85 mM/void volume for a Pharmacia Mono Q® anion-exchange column or 100–150 mM $NaClO_4$ at a rate of 1.7 mM/void volume for a Dionex NucleoPac® anion-exchange column was used to elute the RNA. Fractions were analyzed by a HP-1090 HPLC with a Dionex NucleoPac® column. Fractions containing full length product at ≧80% by peak area were pooled.

For a trityl-off large scale synthesis, the crude material was desalted by applying the solution that resulted from quenching of the desilylation reaction to a 53 mL Pharmacia HiLoad 26/10 Q-Sepharose® Fast Flow column. The column was thoroughly washed with 10 mM sodium perchlorate buffer. The oligonucleotide was eluted from the column with 300 mM sodium perchlorate. The eluent was quantitated and an analytical HPLC was run to determine the percent full length material in the synthesis. The eluent was diluted four fold in sterile $H_2O$ to lower the salt concentration and applied to a Pharmacia Mono Q® 16/10 column. A gradient from 10–185 mM sodium perchlorate was run over 4 column. volumes to elute shorter sequences, the full length product was then eluted in a gradient from 185–214 mM sodium perchlorate in 30 column volumes. The fractions of interest were analyzed on a HP-1090 HPLC with a Dionex NucleoPac® column. Fractions containing over 85% full length material were pooled. The pool was applied to a Pharmacia RPC® column for desalting.

For a trityl-on large scale synthesis, the crude material was desalted by applying the solution that resulted from quenching of the desilylation reaction to a 53 mL Pharmacia HiLoad 26/10 Q-Sepharose® Fast Flow column. The column was thoroughly washed with 20 mM $NH_4CO_3H/10\%$ $CH_3CN$ buffer. The oligonucleotide was eluted from the column with 1.5M $NH_4CO_3H/10\%$ acetonitrile. The eluent was quantitated and an analytical HPLC was run to determine the percent full length material present in the synthesis. The oligonucleotide was then applied to a Pharmacia Resource RPC column. A gradient from 20–55% B (20 mM $NH_4CO_3H/25\%$ $CH_3CN$, buffer A=20 mM $NH_4CO_3H/10\%$ $CH_3CN$) was run over 35 column volumes. The fractions of interest were analyzed on a HP-1090 HPLC with a Dionex NucleoPac® column. Fractions containing over 60% full length material were pooled. The pooled fractions were then submitted to manual detritylation with 80% acetic acid, dried down immediately, resuspended in sterile $H_2O$, dried down and resuspended in $H_2O$ again. This material was analyzed on a HP 1090-HPLC with a Dionex NucleoPac® column. The material was purified by anion exchange chromatography as in the trityl-off scheme (vide supra).

Example 6

Ribozyme Activity Assay

Purified 5'-end labeled RNA substrates (15–25-mers) and purified 5'-end labeled ribozymes (~36-mers) were both heated to 95° C., quenched on ice and equilibrated at 37° C., separately. Ribozyme stock solutions were 1 µM, 200 nM, 40 nM or 8 nM and the final substrate RNA concentrations were ~1 nM. Total reaction volumes were 50 µL. The assay buffer was 50 mM Tris-Cl, pH 7.5 and 10 mM $MgCl_2$. Reactions were initiated by mixing substrate and ribozyme solutions at t=0. Aliquots of 5 µL were removed at time points of 1, 5, 15, 30, 60 and 120 m. Each aliquot was quenched in formamide loading buffer and loaded onto a 15% denaturing polyacrylamide gel for analysis. Quantitative analyses were performed using a phosphorimager (Molecular Dynamics).

Example 7

One pot deprotection of RNA

Applicant has shown that aqueous methyl amine is an efficient reagent to deprotect bases in an RNA molecule. However, in a time consuming step (2–24 hrs), the RNA sample needs to be dried completely prior to the deprotection of the sugar 2'-hydroxyl groups. Additionally, deprotection of RNA synthesized on a large scale (e.g., 100 μmol) becomes challenging since the volume of solid support used is quite large. In an attempt to minimize the time required for deprotection and to simplify the process of deprotection of RNA synthesized on a large scale, applicant describes a one pot deprotection protocol (FIG. 12). According to this protocol, anhydrous methylamine is used in place of aqueous methyl amine. Base deprotection is carried out at 65° C. for 15 min and the reaction is allowed to cool for 10 min. Deprotection of 2'-hydroxyl groups is then carried out in the same container for 90 min in a TEA.3HF reagent. The reaction is quenched with 16 mM TEAB solution.

Referring to FIG. 13, hammerhead ribozyme targeted to site A is synthesized using RNA phosphoramadite chemistry and deprotected using either a two pot or a one pot protocol. Profiles of these ribozymes on an HPLC column are compared. The figure shows that RNAs deprotected by either the one pot or the two pot protocols yield similar full-length product profiles. Applicant has shown that using a one pot deprotection protocol, time required for RNA deprotection can be reduced considerably without compromising the quality or the yield of full length RNA.

Referring to FIG. 14, hammerhead ribozymes targeted to site A (from FIG. 13) are tested for their ability to cleave RNA. As shown in the FIG. 14, ribozymes that are deprotected using one pot protocol have catalytic activity comparable to ribozymes that are deprotected using a two pot protocol.

Example 8

Improved protocol for the synthesis of phosphorothioate containing RNA and ribozymes using 5-S-Alkyltetrazoles as Activating Agent The two sulfurizing reagents that have been used to synthesize ribophosphorothioates are tetraethylthiuram disulfide (TETD; Vu and Hirschbein, 1991 *Tetrahedron Letter* 31, 3005), and 3H-1,2-benzodithiol-3-one 1,1-dioxide (Beaucage reagent; Vu and Hirschbein, 1991 supra). TETD requires long sulfurization times (600 seconds for DNA and 3600 seconds for RNA). It has recently been shown that for sulfurization of DNA oligonucleotides, Beaucage reagent is more efficient than TETD (Wyrzykiewicz and Ravikumar, 1994 *Bioorganic Med. Chem.* 4, 1519). Beaucage reagent has also been used to synthesize phosphorothioate oligonucleotides containing 2'-deoxy-2'-fluoro modifications wherein the wait time is 10 min (Kawasaki et al., 1992 *J. Med. Chem*).

The method of synthesis used follows the procedure for RNA synthesis as described herein and makes use of common nucleic acid protecting and coupling groups, such as dimethoxytrityl at the 5'-end, and phosphoramidites at the 3'-end. The sulfurization step for RNA described in the literature is a 8 second delivery and 10 min wait steps (Beaucage and Iyer, 1991 *Tetrahedron* 49, 6123). These conditions produced about 95% sulfurization as measured by HPLC analysis (Morvan et al., 1990 *Tetrahedron Letter* 31, 7149). This 5% contaminating oxidation could arise from the presence of oxygen dissolved in solvents and/or slow release of traces of iodine adsorbed on the inner surface of delivery lines during previous synthesis.

A major improvement is the use of an activating agent, 5-S-ethyltetrazole or 5-S-methyltetrazole at a concentration of 0.25M for 5 min. Additionally, for those linkages which are phosporothioate, the iodine solution is replaced with a 0.05M solution of 3H-1,2-benzodithiole-3-one 1,1-dioxide (Beaucage reagent) in acetonitrile. The delivery time for the sulfurization step is reduced to 5 seconds and the wait time is reduced to 300 seconds.

RNA synthesis is conducted on a 394 (ABI) synthesizer using a modified 2.5 μmol scale protocol with a reduced 5 min coupling step for alkylsilyl protected RNA and 2.5 min coupling step for 2'-O-methylated RNA. A 6.5-fold excess (162.5 μL of 0.1M=32.5 μmol) of phosphoramidite and a 40-fold excess of S-ethyl tetrazole (400 μL of 0.25M=100 μmol) relative to polymer-bound 5'-hydroxyl was used in each coupling cycle. Average coupling yields on the 394 synthesizer, determined by colorimetric quantitation of the trityl fractions, was 97.5–99%. Other oligonucleotide synthesis reagents for the 394 synthesizer: detritylation solution was 2% TCA in methylene chloride; capping was performed with 16% N-Methyl imidazole in THF and 10% acetic anhydride/10% 2,6-lutidine in THF; oxidation solution was 16.9 mM $I_2$, 49 mM pyridine, 9% water in THF. Fisher Synthesis Grade acetonitrile was used directly from the reagent bottle. S-Ethyl tetrazole solution (0.25M in acetonitrile) was made up from the solid obtained from Applied Biosystems. Sulfurizing reagent was obtained from Glen Research.

Average sulfurization efficiency (ASE) is determined using the formula: $ASE=(PS/Total)^{1/n-1}$
where, PS=integrated $^{31}P$ NMR values of the P=S diester Total=integration value of all peaks n=length of oligo Referring to tables V and VI, effects of varying the delivery and the wait time for sulfurization with Beaucage's reagent is described. These data suggest that 5 second wait time and 300 second delivery time is the condition under which ASE is maximum.

Using the above conditions a 36 mer hammerhead ribozyme is synthesized which is targeted to site A. The ribozyme is synthesized to contain phosphorothioate linkages at four positions towards the 5' end. RNA cleavage activity of this ribozyme is shown in FIG. 16. Activity of the phosphorothioate ribozyme is comparable to the activity of a ribozyme lacking any phosphorothioate linkages.

Example 9

Protocol for the synthesis of 2'-N-phtalimido-nucleoside phosphoramidite

The 2'-amino group of a 2'-deoxy-2'-amino nucleoside is normally protected with N-(9-flourenylmethoxycarbonyl) (Fmoc; Imazawa and Eckstein, 1979 supra: Pieken et al., 1991 *Science* 253, 314). This protecting group is not stable in $CH_3CN$ solution or even in dry form during prolonged storage at −20° C. These problems need to be overcome in order to achieve large scale synthesis of RNA.

Applicant describes the use of alternative protecting groups for the 2'-amino group of 2'-deoxy-2'-amino nucleoside. Referring to FIG. 17, phosphoramidite 17 was synthesized starting from 2'-deoxy-2'-aminonucleoside (12) using transient protection with Markevich reagent (Markiewicz *J. Chem. Res.* 1979, S, 24). An intermediate 13 was obtained in 50% yield, however subsequent introduction of N-phtaloyl (Pht) group by Nefken's method (Nefkens, 1960 *Nature* 185, 306), desilylation (15), dimethoxytrytilation (16) and phosphitylation led to phosphoramidite 17. Since overall yield of this multi-step procedure was low (20%)

applicant investigated some alternative approaches, concentrating on selective introduction of N-phtaloyl group without acylation of 5' and 3' hydroxyls.

When 2'-deoxy-2'-amino-nucleoside was reacted with 1.05 equivalents of Nefkens reagent in DMF overnight with subsequent treatment with Et$_3$N (1 hour) only 10–15% of N and 5'(3')-bis-phtaloyl derivatives were formed with the major component being N-Pht-derivative 15. The N,O-bis by-products could be selectively and quantitively converted to N-Pht derivative 15 by treatment of, crude reaction mixture with cat. KCN/MeOH.

A convenient "one-pot" procedure for the synthesis of key intermediate 16 involves selective N-phthaloylation with subsequent dimethoxytrytilation by DMTCl/Et$_3$N and resulting in the preparation of DMT derivative 16 in 85% overall yield as follows. Standard phosphytilation of 16 produced phosphoramidite 17 in 87% yield. One gram of 2'-amino nucleoside, for example 2'-amino uridine (U.S. Biochemicals® part # 77140) was co-evaporated twice from dry dimethyl formamide (Dmf) and dried in vacuo overnight. 50 mls of Aldrich sure-seal Dmf was added to the dry 2'-amino uridine via syringe and the mixture was stirred for 10 minutes to produce a clear solution. 1.0 grams (1.05 eq.) of N-carbethoxyphthalimide (Nefken's reagent, 98% Jannsen Chimica) was added and the solution was stirred overnight. Thin layer chromatography (TLC) showed 90% conversion to a faster moving products (10% ETOH in CHCl$_3$) and 57 µl of TEA (0.1eq.) was added to effect closure of the phthalimide ring. After 1 hour an additional 855 µl (1.5 eq.) of TEA was added followed by the addition of 1.53 grams (1.1 eq.) of DMT-Cl (Lancaster Synthesis®, 98%). The reaction mixture was left to stir overnight and quenched with ETOH after TLC showed. greater than 90% desired product. Dmf was removed under vacuum and the mixture was washed with sodium bicarbonate solution (5% aq., 500 mls) and extracted with ethyl acetate (2×200 mls). A 25 mm×300 mm flash column (75 grams Merck flash silica) was used for purification. Compound eluted at 80 to 85% ethyl acetate in hexanes (yield: 80% purity: >95% by $^1$HNMR). Phosphoramidites were then prepared using standard protocols described above.

Figure 1:
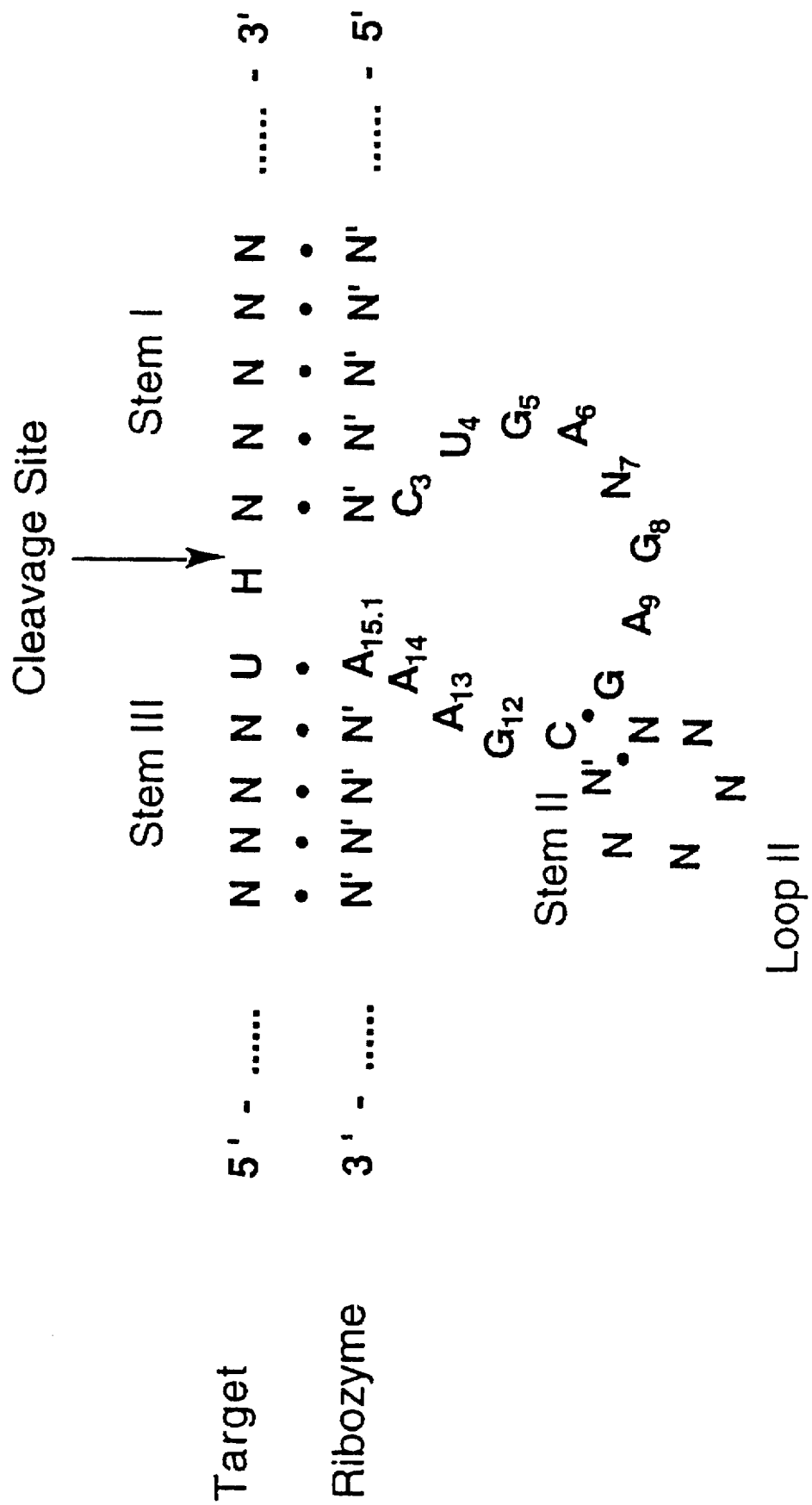
FIG. 1 is a diagrammatic representation of the hammerhead ribozyme domain (SEQ ID Nos. 1 and 2) known in the art. Stem II can be ≧2 base-pairs long.
Figure 2B:
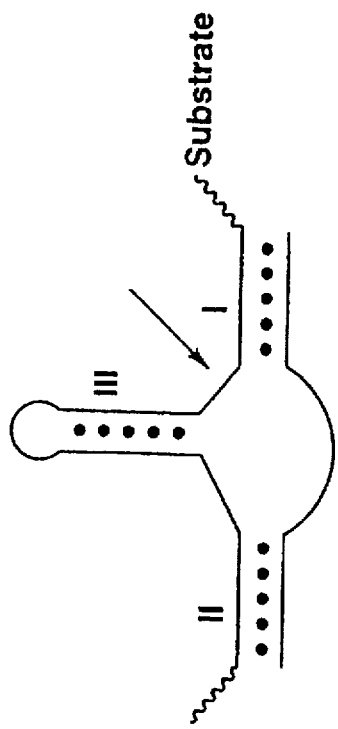
FIG. 2b is a diagrammatic representation of the hammerhead ribozyme as divided by Uhlenbeck (1987, Nature, 327, 596–600) into a substrate and enzyme portion.
Figure 2D:
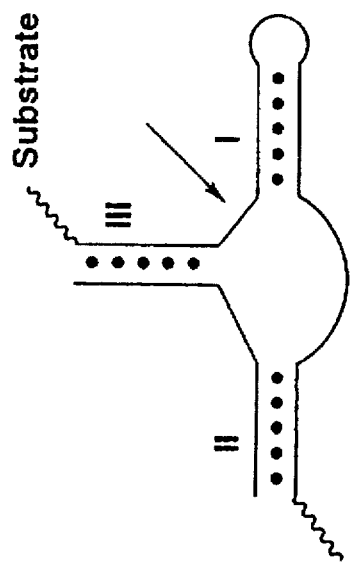
FIG. 2d is a similar diagram showing the hammerhead divided by Jeffries and Symons (1989, Nucl, Acids. Res., 17, 1371–1371) into two portions.
Figure 2A:
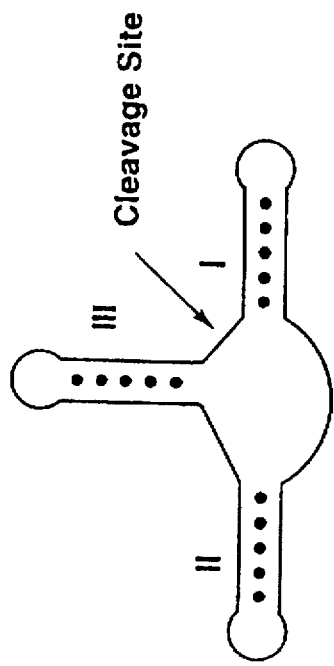
FIG. 2a is a diagrammatic representation of the hammerhead ribozyme domain known in the art.
Figure 2C:
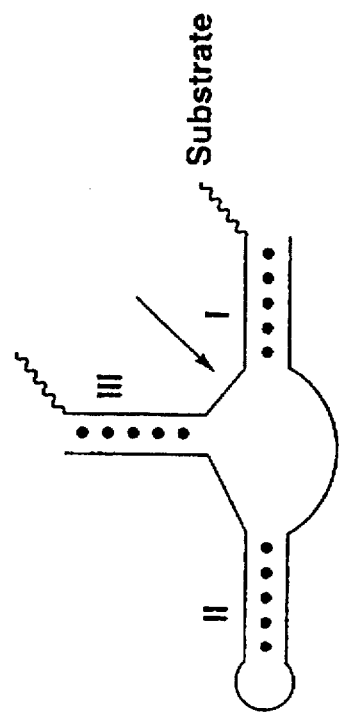
FIG. 2c is a similar diagram showing the hammerhead divided by Haseloff and Gerlach (1988, Nature, 334, 585–591) into two portions.

With phosphoramidite 17 in hand applicant synthesized several ribozymes with 2'-deoxy-2'-amino modifications. Analysis of the synthesis demonstrated coupling efficiency in 97–98% range. RNA cleavage activity of ribozymes containing 2'-deoxy-2'-amino-U modifications at U4 and/or U7 positions (see FIG. 1), wherein the 2'-amino positions were either protected with Fmoc or Pht, was identical. Additionally, complete deprotection of 2'-deoxy-2'-amino-Uridine was confirmed by base-composition analysis. The coupling efficiency of phosphoramidite 17 was not effected over prolonged storage (1–2 months) at low temperatures.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.

TABLE I-continued

Characteristics of Ribozymes

RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (Figure 1)
Hairpin Ribozyme Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent.
Hepatitis Delta Virus (HDV) Ribozyme Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV.
Neurospora VS RNA Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospara VS RNA.

TABLE II

Large-Scale Synthesis

| Sequence | Activator [Added/Final] (min) | Amidite [Added/Final] (min) | Time* | % Full Length Product |
| --- | --- | --- | --- | --- |
| A$_9$T | T [0.50/0.33] | [0.1/0.02] | 15 m | 85 |
| A$_9$T | S [0.25/0.17] | [0.1/0.02] | 15 m | 89 |
| (GGU)$_3$GGT | T [0.50/0.33] | [0.1/0.02] | 15 m | 78 |
| (GGU)$_3$GGT | S [0.25/0.17] | [0.1/0.02] | 15 m | 81 |
| C$_9$T | T [0.50/0.33] | [0.1/0.02] | 15 m | 90 |
| C$_9$T | S [0.25/0.17] | [0.1/0.02] | 15 m | 97 |
| U$_9$T | T [0.50/0.33] | [0.1/0.02] | 15 m | 80 |
| U$_9$T | S [0.25/0.17] | [0.1/0.02] | 15 m | 85 |
| A (36-mer) | T [0.50/0.33] | [0.1/0.02] | 15/15 m | 21 |
| A (36-mer) | S [0.25/0.17] | [0.1/0.02] | 15/15 m | 25 |
| A (36-mer) | S [0.50/0.24] | [0.1/0.03] | 15/15 m | 25 |
| A (36-mer) | S [0.50/0.18] | [0.1/0.05] | 15/15 m | 38 |
| A (36-mer) | S [0.50/0.18] | [0.1/0.05] | 10/5 m | 42 |

*Where two coupling times are indicated the first refers to RNA coupling and the second to 2'-O-methyl coupling. S = 5-S-Ethyltetrazole, T = tetrazole activator. A is 5' -ucu ccA UCU GAU GAG GCC GAA AGG CCG AAA Auc ccu -3' where lowercase represents 2' -O-methylnucleotides.

TABLE III

Base Deprotection

| Sequence | Deprotection Reagent | Time (min) | T °C. | % Full Length Product |
|---|---|---|---|---|
| iBu(GGU)₄ | NH₄OH/EtOH | 16 h | 55 | 62.5 |
| | MA | 10 m | 65 | 62.7 |
| | AMA | 10 m | 65 | 74.8 |
| | MA | 10 m | 55 | 75.0 |
| | AMA | 10 m | 55 | 77.2 |
| iPrP(GGU)₄ | NH₄OH/EtOH | 4 h | 65 | 44.8 |
| | MA | 10 m | 65 | 65.9 |
| | AMA | 10 m | 65 | 59.8 |
| | MA | 10 m | 55 | 61.3 |
| | AMA | 10 m | 55 | 60.1 |
| C₉U | NH₄OH/EtOH | 4 h | 65 | 75.2 |
| | MA | 10 m | 65 | 79.1 |
| | AMA | 10 m | 65 | 77.1 |
| | MA | 10 m | 55 | 79.8 |
| | AMA | 10 m | 55 | 75.5 |
| A (36-mer) | NH₄OH/EtOH | 4 h | 65 | 22.7 |
| | MA | 10 m | 65 | 28.9 |

TABLE IV

2'-O-Alkylsilyl Deprotection

| Sequence | Deprotection Reagent | Time (min) | T °C. | % Full Length Product |
|---|---|---|---|---|
| A₉T | TBAF | 24 h | 20 | 84.5 |
| | 1.4 M HF | 0.5 h | 65 | 81.0 |
| (GGU)₄ | TBAF | 24 h | 20 | 60.9 |
| | 1.4 M HF | 0.5 h | 65 | 67.8 |
| C₁₀ | TBAF | 24 h | 20 | 86.2 |
| | 1.4 M HF | 0.5 h | 65 | 86.1 |
| U₁₀ | TBAF | 24 h | 20 | 84.8 |
| | 1.4 M HF | 0.5 h | 65 | 84.5 |
| B (36-mer) | TBAF | 24 h | 20 | 25.2 |
| | 1.4 M HF | 1.5 h | 65 | 30.6 |
| A (36-mer) | TBAF | 24 h | 20 | 29.7 |
| | 1.4 M HF | 1.5 h | 65 | 30.4 |

B is 5'- UCU CCA UCU GAU GAG GCC GAA AGG CCG AAA AUC CCU

TABLE V

NMR Data for UC Dimers containing Phosphorothioate Linkage

| Synthesis # | Type | Delivery | Eq. | Wait | ASE (%) |
|---|---|---|---|---|---|
| 3524 | ribo | 2 × 3s | 10.4 | 2 × 100s | 95.9 |
| 3525 | ribo | 2 × 3s | 10.4 | 2 × 75s | 92.6 |
| 3530 | ribo | 2 × 3s | 10.4 | 2 × 75s | 92.1 |
| 3526 | ribo | 1 × 5s | 08.6 | 1 × 300s | 100.0 |
| 3578 | ribo | 1 × 5s | 08.6 | 1 × 250s | 100.0 |
| 3529 | ribo | 1 × 5s | 08.6 | 1 × 150s | 73.7 |

TABLE VI

NMR Data for 15-mer RNA containing Phosphorothioate Linkages

| Synthesis # | Type | Delivery | Eq. | Wait | ASE (%) |
|---|---|---|---|---|---|
| 3581 | ribo | 1 × 5s | 08.6 | 1 × 250s | 99.6 |
| 3663 | ribo | 2 × 4s | 13.8 | 2 × 300s | 100.0 |
| 3582 | 2'-O—Me | 1 × 5s | 08.6 | 1 × 250s | 99.7 |
| 3668 | 2'-O—Me | 2 × 4s | 13.8 | 2 × 300s | 99.8 |
| 3682 | 2'-O—Me | 1 × 5s | 08.6 | 1 × 300s | 99.8 |

---

We claim:

1. Method for one pot deprotection of RNA comprising, contacting a protected base with anhydrous methyl amine at between 60° C.–70° C. for at least 5 min, cooling the resulting mixture and contacting said mixture with TEA-3HF reagents under conditions which remove a protecting group of the 2'-hydroxyl position.

2. Method of claim 1 wherein said RNA is enzymatically active.

3. Method for one pot deprotection of RNA comprising, contacting a protected base with anhydrous ethyl amine at between 60° C.–70° C. for at least 5 min, cooling the resulting mixture and contacting said mixture with TEA-3HF reagents under conditions which remove a protecting group of the 2'-hydroxyl position.

* * * * *